(12) United States Patent
Sharma et al.

(10) Patent No.: US 7,803,351 B2
(45) Date of Patent: *Sep. 28, 2010

(54) BLOOD BRAIN BARRIER PERMEATION PEPTIDES

(75) Inventors: Vijay Sharma, Wildwood, MO (US); David Piwnica-Worms, Ladue, MO (US)

(73) Assignee: Washington University, St. Louis, MO (US)

( * ) Notice: Subject to any disclaimer, the term of this patent is extended or adjusted under 35 U.S.C. 154(b) by 1440 days.

This patent is subject to a terminal disclaimer.

(21) Appl. No.: 11/207,954

(22) Filed: Aug. 19, 2005

(65) Prior Publication Data
US 2006/0039859 A1 Feb. 23, 2006

Related U.S. Application Data

(60) Provisional application No. 60/603,403, filed on Aug. 20, 2004.

(51) Int. Cl.
*A61K 51/00* (2006.01)
*A61M 36/14* (2006.01)

(52) U.S. Cl. .................. 424/1.69; 424/1.11; 424/1.65; 534/14

(58) Field of Classification Search .............. 424/1.11, 424/1.65, 1.69, 1.81, 1.85, 1.89, 1.49, 1.73, 424/9.1, 9.3, 9.4, 9.5; 534/7, 10–16; 530/300
See application file for complete search history.

(56) References Cited

U.S. PATENT DOCUMENTS

| 4,526,714 | A | 7/1985 | Feijen et al. |
| 4,554,101 | A | 11/1985 | Hopp |
| 5,747,641 | A | 5/1998 | Frankel et al. |
| 6,348,185 | B1 * | 2/2002 | Piwnica-Worms ......... 424/1.69 |
| 6,589,503 | B1 * | 7/2003 | Piwnica-Worms ......... 424/1.69 |
| 6,696,039 | B2 | 2/2004 | Kung et al. |
| 7,306,783 | B2 * | 12/2007 | Piwnica-Worms ......... 424/1.69 |
| 7,306,784 | B2 * | 12/2007 | Piwnica-Worms ......... 424/1.69 |

FOREIGN PATENT DOCUMENTS

EP 0213523 12/1990

OTHER PUBLICATIONS

Kurihara et al (Bioconjugate Chemistry, 2000, vol. 11, No. 3, pp. 380-386).*
Adkison et al. (1994) Contribution of Probenecid-Sensitive Anion Transport Processes at the BraIN Capillary Endothelium and Choroid Plexus to the Efficient Efflux of Valproic Acid from the Central Nervous System, *J. Pharmacol Exp. Ther*. 268, 797-805.
Alberico et al. (1998) Use of onium salt-based coupling reagents in peptide synthesis. *J Org Chem*, 63, 9678-9683.
Arpicco et al. (1997) New coupling reagents for the preparation of disulfide cross-linked conjugates with increased stability. *Bioconjug Chem*, 8, 327-337.
Babich et al. (1995) Effect of "co-ligand" on the biodistribution of 99mTc-labeled hydrazino nicotinic acid derivatized chemotactic peptides. *Nucl Med Biol*, 22, 25-30.
Ball et al., Consensus Recommendations for the Postmortem Diagnosis of Alzheimer's Disease, Neurbiol. of Aging, 1997, S1-S2, vol. 18.
Barany et al. (1992) Biopolymer syntheses on novel polyethylene glycolpolystyrene (PEG-PS) graft supports, pp. 603-604. In Peptides. Chem Biol, Proc. Am. Pept. Symp. (12$^{th}$).
Beyer et al.(1998) Synthesis and in vitro efficacy of transferrin conjugates of the anticancer drug chlorambucil. *J Med Chem*, 41, 2701-2708.
Blomberg et al. (1999) Terbium and rhodamine as labels in a homogeneous time-resolved fluorometric energy transfer assay of the β subunit of human chorionic gonadotropin in serum. *Clin Chem*, 45, 855-861.
Bullok et al. (2002) Characterization of Novel Histidine-Tagged Tat-Peptide Complexes Dual-Labeled with $^{99m}$Tc-Tricarbonyl and Fluorescein for Scintigraphy and Fluorescence Microscopy. *Bioconjugate Chem.*, 13, 1226-1237.
Bush (2003) The Metallobiology of Alzheimer's Disease, *Trends in Neurosciences* 26, 207-214.
De Graaf et al. (1996) P-Glycoprotein Confers Methotrexate Resistance in 3T6 Cells with Deficient Carrier-Mediated Methotrexate Uptake, *Proc. Natl. Acad. Sci. USA*, 93, 1238-1242.
Deguchi et al. (1998) Retention of Biologic Activity of Human Epidermal Growth Factor Following Conjugation to a Blood-Brain Barrier Drug Delivery Vector via an Extended Poly(ethylene glycol) Linker. *Bioconjug .Chem.*, 10, 32-37.
Demattos et al. (2002) Clusterin promotes amyloid plaque formation and is critical for neuritic toxicity in a mouse model of Alzheimer's disease. *Proc Natl Acad Sci USA*, 99, 10843-10848.
Dezutter et al. (1999) Preparation of 99mTc-N2S2 conjugates of Chrysamine G:potential probes for beta-amyloid protein of Alzheimer's disease. *J label Compd Radiopharm*, 42, 309-324.
Dezutter et al. (1999) A probe for b-amyloid protein of Alzheimer's disease. *Eur J Nucl Med*, 26, 1392-1399.
Dirven et al. (1996) Glutathione conjugation of alkylating cytostatic drugs with a nitrogen mustard group and the role of glutathione S-Transferases. *Chem Res Toxicol*, 9, 351-360.
Dishino et al. (1983) Relationship between lipophilicity and brain extraction of C-11-labeled radiopharmaceuticals. *J Nuc Med*, 24, 1030-1038.
Dovey et al. (2001) Functional Gamma-Secretase Inhibitors Reduce Beta-Amyloid Peptide Levels in Brain, *J. Neurochem*. 76, 173-181.
Drouillat et al. (1998) Novel liposaccharide conjugates for drug and peptide delivery. *J. Pharm. Sci.*, 87, 25-30.

(Continued)

*Primary Examiner*—D L Jones
(74) *Attorney, Agent, or Firm*—Sonnenschein Nath & Rosenthal LLP

(57) ABSTRACT

Novel blood-brain barrier permeant amyloid-targeting peptides and peptide conjugates are described. The peptide conjugates include a radioisotope or other label in a stable complex that translocates across brain capillary endothelial cell monolayers. The labeled peptide conjugate binds to amyloid plaques (Aβ) associated with Alzheimer's disease, and is useful for the targeted delivery of therapeutic and diagnostic molecules into the brain.

12 Claims, 12 Drawing Sheets

OTHER PUBLICATIONS

Eckelman (1995) Radiolabeling with technetium-99m to study high-capacity and low-capacity biochemical systems. *Eur J Nucl Med*, 22, 249-263.

Frisch et al. (1996) Synthesis of short polyoxyethylene-based heterobifunctional cross-linking reagents. Application to the coupling of peptides to liposomes. *Bioconjug Chem*, 7, 180-186.

Games (1995) Alzheimer-type neuropathology in transgenic mice overexpressing V717F β-amyloid precursor protein. *Nature*, 373, 523-527.

Gammon et al. (2003) Quantitative Analysis of Permeation Peptide Complexes Labeled with Technetium-99m: Chiral and Sequence-Specific Effects on Net Cell Uptake, *Bioconjugate Chem* 14., 368-375.

Grummon et al. (1995) Synthesis, Characterization and Crystal Structures of Technetium(V)-Oxo Complexes Useful in Nuclear Medicine. 1. Complexes of Mercaptoacetylglycylglycylglycine (MAG3) and Its Methyl Ester Derivative (MAG3Ome). *Inorg Chem*, 34, 1764-1772.

Han et al. (1996) Technetium complexes for quantification of brain amyloid. *J Am Chem Soc*, 118, 4506-4508.

Han et al. (1996) Technetium Complexes for the Quantitation of Brain Amyloid, *J. Am. Chem. Soc.* 118, 4506-4507.

Hedaya et al. (1989) Effect of Probenecid on the Renal and Nonrenal Clearances of Zidovudine and Its Distribution into Cerebrospinal Fluid in the Rabbit, *J. Pharma. Sci.* 78, 716-722.

Herman et al. (1995) Novel Hexakis(areneisonitrile)technetium(I) Complexes as Radioligands Targetd to the Multidrug Resistance P-Glycoprotein, *J. Med. Chem.* 38, 2955-2963.

Holtzman et al. (2000) Apolipoprotein E isoform-dependent amyloid deposition and neuritic degeneration in a mouse model of Alzheimer's disease. *Proc Natl Acad Sci USA*, 97, 2892-2897.

Hom et al. (1997) Technetium-99m-labeled receptor-specific small-molecule radiopharmaceuticals: recent developments and encouraging results. *Nucl Med Biol*, 24, 485-498.

Houghten (1985) General method for the rapid solid-phase synthesis of large numbers of peptides: specificity of antigen-antibody interaction at the level of individual amino acids. *Proc. Natl. Acad. Sci. USA*, 82, 5131-5135.

Hsiao et al. (1996) Correlative memory deficits, Aβ elevation, and amyloid plaques in transgenic mice. *Science*, 274, 99-102.

Jamieson et al. (1999) Structural and Kinetic studies of a cisplatin-modified DNA Icosamer binding to HMG1 Domain B. *J Biol Chem*, 274, 12346-12354.

Jurisson et al. (1993) Coordination compounds in nuclear medicine. *Chem Rev*, 93, 1137-1156.

Kempe et al. (1996) CLEAR: A Novel Family of Highly Cross-Linked Polymeric Supports for Solid-Phase Peptide Synthesis. *J. Am. Chem. Soc.*, 118, 7083-7093.

Klunk et al. (2002) Imaging Ab plaques in living transgenic mice with multiphoton microscopy and methoxy-X04, a systemically administered congo red derivative. *J Neuropathol Exp Neurol*, 61, 797-805.

Klunk et al. (2001) Uncharged thioflavin-T derivatives bind to amyloid-beta protein with high affinity and readily enter the brain. *Life Sci*, 69, 1471-1484.

Kowall et al. (1992) In vivo neurotoxicity of b-amyloid (1-40) and b(25-35) fragment. *Neurobiol Aging*, 13, 537-542.

Kung et al. (2002) IMPY: an improved thioflavin-T derivative for in vivo labelling of b-amyloid plaques. *Brain Res*, 956, 202-210.

Kyte et al. (1982) A simple method of displaying the hydropathic character of a protein. *J. Mol. Biol.*, 157, 105-132.

Lansbury (1996) A reductionist view of Alzheimer's disease. *Acc Chem Res*, 29, 317-321.

Lee et al. (2002) Imaging Brain Amyloid of Alzheimer Disease In Vivo in Transgenic Mice with an Aβ Peptide Radiopharmaceutical, *J. Cerebral Blood Flow Metabolism* 22, 223-231.

Lee et al. (2003) Dimethylamin-Fluorenes: Ligands for Detecting—Amyloid Plaques in the Brain, *Nuclear Med Biol.* 30, 573-580.

Lemere et.al. (1996) The E280A presenilin1 Alzheimer mutation produces increased Aβ42 deposition and severe cerebellar pathology. *Nature Med*, 2, 1146-1148.

Lemere et al. (1996) Sequence of deposition of heterogenous amyloid β-peptides and Apo-E in Down Syndrome: Implications for initial events in amyloid plaque formation. *Neurobiol Disease*, 3, 16-32.

Li et al. (1999) 3-(Diethoxyphosphoryloxy)-1,2,3- benzotriazin-4(3H)-one (DEPBT): A new coupling reagent with remarkable resistance to racemization. *Organic Letters*, 1, 91-94.

Li et al. (1999) A calcium-sensitive magnetic resonance imaging contrast agent. *J Am Chem Soc*, 121, 1413-1414.

Lin et al. (1988) Synthesis of a biological active tumor growth factor from the predicted DNA sequence of Shope fibroma virus. *Biochemistry*, 27, 5640-5645.

Lister-James et al. (1996) Thrombus imaging with a technetium-99m-labeled activated platelet receptor-binding peptide. *J Nucl Med*, 37, 775-781.

Lister-James et al. (1997) Pharmacokinetic considerations in the development of peptide-based imaging agents. *Q J Nucl Med*, 41, 111-118.

Lister-James et al. (1997) Pre-clinical evaluation of technetium-99m platelet receptor-binding peptide. *J Nucl Med*, 38, 105-111.

Liu et al. (1996) Modulation of multidrug resistance gene (mdr-1) with antisense oligodeoxynucleotides. *Clin Sci (Lond)*, 91, 93-98.

Liu et al. (1999) $^{99m}$Tc-labeled small peptides as diagnostic radiopharmaceuticals. *Chem Rev*, 99, 2235-2268.

Majocha et al. (1992) Development of monoclonal antibody specific for b/A4 amyloid in Alzheimer disease brain for application to invivo imaging of amyloid angiopathy. *J Nucl Med*, 33, 2184-2189.

McKhann et. Al. (1984) Clinical diagnosis of Alzheimer's disease:a report of the NINCDS-ADRDA work group. *Neurology*, 34, 939-944.

Meegalla et al. (1997) Synthesis and characterization of technetium-99m-labeled tropanes as dopamine transporter-imaging agents. *J. Med. Chem.*, 40, 9-17.

Meldal (1992) Pega: a flow stable polyethylene glycol dimethyl acrylamide copolymer for solid phase synthesis. *Tetrahedron Lett.*, 33, 3077-3080.

Merrifield et al. (1982) Synthesis of the antibacterial peptide cecropin A (1-33). *Biochemistry*, 21, 5020-5031.

Mroczkowsa et al. (2000) Blood-brain barrier controls carnitine levels in the brain: A study on a model system with RBE4 cells. *Biochem Biophys Res Commun*, 267, 433-437.

Ono et al. (2003) C-Labeled Stilbene Derivaties as Aβ-Aggregate-Specific PET Imaging Agents for Alzheimer's Disease, *Neuclear Med Biol.* 30, 565-571.

Ooie et al. (1997) Kinetic Evidence for Active Efflux Transport Across the Blood-Brain Barrier of Quinolone Antibiotics, *J. Pharmacol Exp Thera.* 283, 293-304.

Papadopoulos et al. (1993) Correlation of lipophilicity to biodistribution of 99mTc-labelled aminothiols. *Nucl. Med. Biol.*, 20, 101-104.

Poduslo et al. (2002) Molecular targeting of Alzheimer's amyloid plaques for contrast-enhanced magnetic resonance imaging. *Neurobiol Disease*, 11, 315-329.

Polyakov et al. (2000) Novel Tat-peptide chelates for direct transduction of technetium-99m and rhenium into human cells for imaging and radiotherapy. *Bioconjug Chem*, 11, 762-771.

Prantner et al. (2003) Synthesis and characterization of a Gd-DOTA D-permeation peptide for magnetic resonance relaxation enhancement of intracellular targets. *Molec Imaging*, 2, 333-341.

Rajogopalan et al. (1997) Preparation, characterization, and biological evaluation of technetium(V) and rhenium(V) complexes of novel heterocyclic tetradentate $N_3S$ ligands. *Bioconjugate Chem*, 8, 407-415.

Reisberg et al. (2003) Is Memantine a Breakthrough in the Treatment of Moderate-to-Severe Alzheimer's Disease?, *Expert Opinion*, 1857-1860.

Scheuner et al. (1996) Secreted amyloid β-protein similar to that in the senile plaques of Alzheimer's disease is increased in vivo by the presenilin 1 and 2 and APP mutations linked to familial Alzheimer's disease. *Nature Med*, 2, 864-870.

Schinkel et al. (1994) Disruption of the Mouse *mdr1a* P-Glycoprotein Gene Leads to a Deficiency in the Blood-Brain Barrier and to Increased Sensitivity to Drugs, *Cell.* 77, 491-502.

Schinkel et al. (1995) Absence of the mdr1a P-Glycoprotein in Mice Affects Tissue Distribution and Pharmacokinetics of Dexamethasone, Digoxin, and Cyclosporin A, *J. Clin. Invest.* 96, 1698-1705.

Schlageter et al. (1987) Examination of Blood-Brain Barrier Permeability ni Dementia of the Alzheimer Type with [$^{68}$Ga]EDTA and Positron Emission Tomography, *J. Cerebral Blood Flow Metabolism* 7, 1-8.

Schumock (1998) Economic Considerations in the Treatment and Management of Alzheimer's Disease, *Am. J. Health-Syst. Pharm.* 55, S17-S21.

Selkoe (1997) Alzheimer's disease: genotype, phenotype, and treatments. *Science*, 275, 630-631.

Selkoe (1996) Amyloid β-Protein and the Genetics of Alzheimer's Disease. *J. Biol. Chem.*, 271, 18295-18298.

Sharma et al. (2002) Molecular Imaging of Gene Expression and Protein Function In Vivo with PET and SPECT. *J. Magnetic Resonance Imag.*, 16, 336-351.

Skovronsky et al. (2000) In vivo detection of amyloid plaques in a mouse model of Alzheimer's disease. *Proc Natl Acad Sci USA*, 97, 7609-7614.

Suzuki et al. (1989) Transport of Imipenem, A Novel Carbapenem Antibiotic, in the Rat Central Nervous System, *J. Pharmacol Exp. Thera.* 250, 979-984.

Tariot et al. (2004) Memantine Treatment in Patients with Moderate to Severe Alzheimers Disease Already Receive Donepezil, *JAMA* 291, 317-324.

Teller (1996) Presence of soluble amyloid β-peptide precedes amyloid plaque formation in Down's syndrome. *Nature Med*, 2, 93-95.

Tjernberg et al. (1997) Controlling amyloid b-fibril formation with protease-stable ligands. *J Biol Chem*, 272, 12601-12605.

Trimble et al. (1997) Use of designed peptide linkers and recombinant hemoglobin mutants for drug delivery: In vitro release of an angiotensin II analog and kinetic modeling of delivery. *Bioconjug Chem*, 8, 416-423.

Ubarretexna-Belandia et al. (1999) Outer membrane phospholipase A is dimeric in phospholipid bilayers: A cross-linking and fluorescence resonance energy transfer study. *Biochemistry*, 38, 7398-7405.

Violini et al. (2002) Evidence for a plasma membrane-mediated permeability barrier to Tat basic domain in well-differentiated epithelial cells: lack of correlation with heparan sulfate. *Biochemistry*, 41, 12652-12661.

Vorbrodt et al. (1997) Immunocytochemial Evaluation of Blood-Brain Barrier to Endogenous Albumin in Scrapie-Infected Mice, *Acta Neuropathol.* 93, 341-348.

Wadghiri et al. (2003) Detection of Alzheimer's amyloid in transgenic mice using magnetic resonance microimaging. *Magn Reson Med*, 50, 293-302.

Walker et al. (1994) Labeling of cerebral amyloid in vivo with a monoclonal antibody. *J Neuropathol Exp Neurol*, 53, 377-383.

Wang et al. (2002) Synthesis and $^{11}$C-Labelling of (E,E)-1,(3',4'-dihydroxystyryl)-4-(3'-methoxy-4'-hydroxystyryl) benezene for PET Imaging of Amyloid Deposits, *J. Label Compd Radiopharm.* 45, 647-664.

Wang et al. (1995) Zidovudine Transport in the Rabbit Brain During Intravenous and Intracerebroventricular Infusion, *J. Pharma. Sci.* 84, 871-876.

Weiner (1997) Alzheimer's disease: diagnosis and treatment. *Harvard Rev. Psychiatry*, 4, 306-316.

Weissleder et al. (2000) In vivo magnetic resonance imaging of transgene expression. *Nat Med*, 6, 351-355.

Wengenack et al. (2000) Targeting Alzheimer amyloid plaques invivo. *Nat Biotech*, 18, 868-872.

Wong et al. (1997) Rhenium(V) and technetium(V) oxo complexes of an N$_2$N'S peptidic chelator: evidence of interconversion between the *syn* and *anti* conformations. *Inorg Chem*, 36, 5799-5808.

Yanker (1996) Mechanisms of neuronal degeneration in Alzheimer's disease. *Neuron*, 16, 921-932.

Zhen et al. (1999) Synthesis and amyloid binding properties of rhenium complexes: preliminary progress towards a reagent for SPECT imaging of Alzheimer's disease brain. *J Med Chem*, 42, 2805-2815.

Zhuang et al. (2003) Structure-activity relationships of imidazo[1,2-a]pyridines as ligands for detecting amyloid plaques in the brain. *J Med Chem*, 46, 237-243.

\* cited by examiner

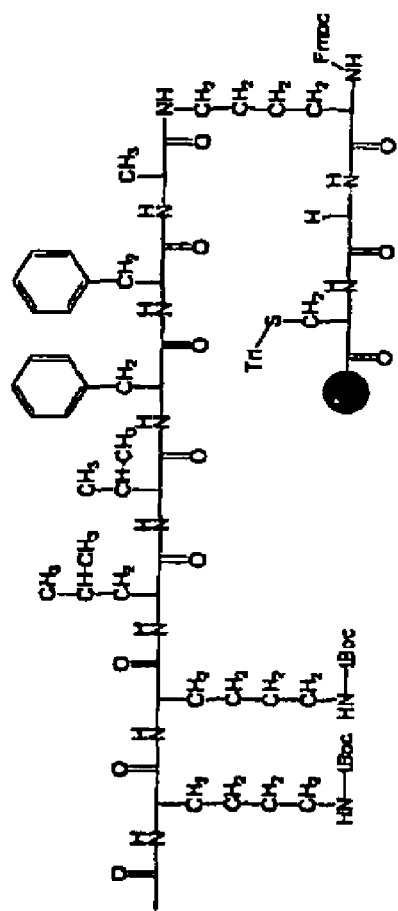
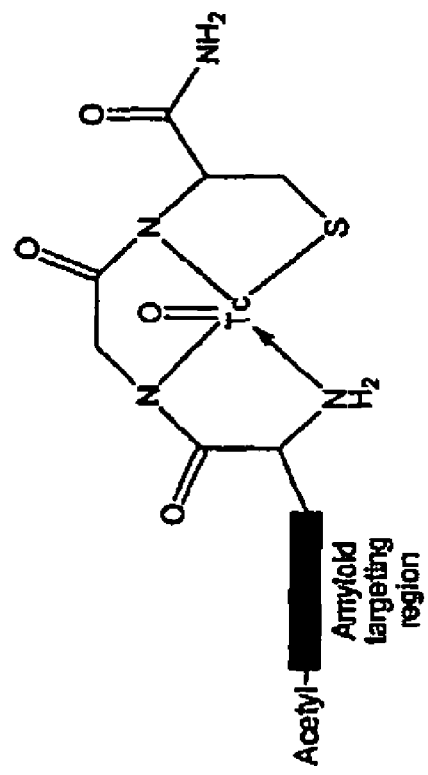
Figure 1b
Figure 1a

BLOOD BRAIN BARRIER PERMEATION PEPTIDES

CROSS-REFERENCE TO RELATED APPLICATIONS

This application claims the benefit of prior filed U.S. provisional patent application Ser. No. 60/603,403, filed Aug. 20, 2004, the specifications of which are herein incorporated by reference in their entireties.

STATEMENT REGARDING FEDERALLY SPONSORED RESEARCH OR DEVELOPMENT

This invention was made in part with Government support under National Institutes of Health Grant CA 82841. The Government has certain rights in the invention.

REFERENCE TO A SEQUENCE LISTING

The Sequence Listing, which is a part of the present disclosure, includes a text file comprising nucleotide and/or amino acid sequences of the present invention on a floppy disk. The subject matter of the Sequence Listing is incorporated herein by reference in its entirety.

BACKGROUND OF THE INVENTION

1. Field of the Invention

The present invention broadly relates to the fields of medical imaging, diagnostics, and pharmaceutical therapy.

2. Description of the Related Art

Radiopharmaceuticals

In general, radiopharmaceuticals provide vital information that aids in the diagnosis and therapy of a variety of medical diseases (Hom and Katzenellenbogen, 1997). Radiopharmaceuticals relay data on tissue shape, biochemical function, and localization within the body by use of radionuclides which act as imaging agents. Radionuclides include free chemical species, such as the gas $^{133}$Xe, or the ions $^{123}$I- and $^{201}$Tl-, which are covalently or coordinately bound to a larger organic or inorganic chemical moiety. Images are generated from the signal arising from radioactive decay of the nuclide which is distributed in tissues according to the properties of the larger moiety to which the radionuclide is bound. Radionuclides most commonly used for medical imaging include $^{11}$C ($t_{1/2}$=20.4 min), $^{13}$N ($t_{1/2}$=9.97 min), $^{15}$O ($t_{1/2}$=2.03 min), $^{18}$F ($t_{1/2}$=109.7 min), $^{64}$Cu ($t_{1/2}$=12 h), $^{68}$Ga ($t_{1/2}$=68 min), and $^{94m}$Tc ($t_{1/2}$=53 min) for positron emission tomography (PET) and $^{67}$Ga ($t_{1/2}$=68 min), $^{99m}$Tc ($t_{1/2}$=6 h), $^{123}$I ($t_{1/2}$=13 h) and $^{201}$Tl ($t_{1/2}$=73.5 h) for single photon emission computed tomography (SPECT) (Hom and Katzenellenbogen, 1997).

SPECT and PET imaging provide accurate data on radionuclide distribution in the desired target tissue by detection of the gamma photons that result from radionuclide decay. The high degree of spatial resolution of modern commercial SPECT and PET scanners enables images to be generated that map the radionuclide decay events into an image that reflects the distribution of the agent in the body. These images thus contain anatomic and functional information useful in medical diagnosis. Radionuclide decay can also be exploited for therapeutic effect. When radionuclides decay in such a manner as to deposit radiation energy in or near target cells or tissues, therapeutically relevant doses of radioactivity are deposited within the tissues.

The tissue specificity or targeting properties of radiopharmaceuticals often depends largely on overall size, charge, or physical state (Hom and Katzenellenbogen, 1997). Certain radiopharmaceuticals have been synthesized that demonstrate specific binding to, for example, a specific hormone, neurotransmitter, cell surface or drug receptor, enzyme, or high affinity transport systems. When select receptors, enzymes and the like are known to be involved in the regulation of a wide variety of vital bodily functions, targeted imaging agents such as those combining a chemical constituent having specific binding properties with a radionuclide are especially useful in the diagnosis or staging of a variety of disease states. For example, diseases in which such receptors are functioning abnormally or are distributed in an abnormal fashion are especially amenable to diagnosis using such radiopharmaceuticals. The success of therapy of such diseases can also be monitored using radiopharmaceuticals (Hom and Katzenellenbogen, 1997).

Recent advances in molecular, structural and computational biology have begun to provide insights into the structure of molecular targets, receptors and enzymes and these insights can be used to design various targeting molecules, or ligands. The localization of molecular targets within tissues also directly impacts the development of new radiopharmaceuticals. Most importantly, the location of a receptor or enzyme activity in the body (i.e., peripheral sites versus brain sites), and the receptor's subcellular location (i.e., on the cell surface versus intracellular) determines whether a radiopharmaceutical injected intravenously will need to traverse one or more membrane and cellular barriers to reach the target. Moreover, the structure of the molecular target, its localization in tissues, and the nature of the target's interaction with its natural ligand are all factors that help determine the degree to which large ligands or ligands with large substituents may be tolerated (Han et al., 1996). For example, radiopharmaceuticals that target cell surface receptors encounter no membrane barriers to reach their target. Thus, natural ligands for these targets can be relatively large, and are often charged and consequently large radiopharmaceutical molecules can be used for such targets. Conversely, a radiopharmaceutical which must reach a target within the central nervous system must traverse the blood-brain barrier formed by endothelial cells of the brain. Thus, design of radiopharmaceuticals for targets within the central nervous system favors minimal size and molecular weight (Dishino, 1983; Eckelman, 1995; Hom and Katzenellenbogen, 1997; Papadopoulos et al., 1993).

A focus of recent research has been the development of radiopharmaceuticals targeting cell surface receptors whose natural ligands are peptides. Peptide-based radiopharmaceuticals include a derivatizing group or chelating structure coupled to a peptide, with a radionuclide held by the chelating structure. Peptide-based imaging agents have been described (Lister-James et al., 1997a; Lister-James et al., 1997b; Polyakov et al., 2000), especially those that incorporate technetium-99m (Tc-99m) as the radionuclide, the most commonly used isotope in medical imaging. A variety of metal chelation systems have been developed for synthesis of radioisotopic and magnetic resonance peptide-based imaging agents. Peptide-based agents conventionally target extracellular or externally oriented membrane bound receptors (Hom and Katzenellenbogen, 1997) because the charge, relatively large size, and pharmacokinetic properties of typical peptide structures do not allow diffusion across the lipid bilayer of the cell plasma membrane of cells. For smaller peptides, the size of the added derivatizing group or chelating structure for carrying the radionuclide substantially impacts the in vitro binding and in vivo distribution properties of these compounds (Babich, 1995; Liu et al., 1996). Thus, the design of peptide metal chelates which can report on the functional status or biological activity of targets in the central nervous system is a significant challenge. Until now, peptide-based imaging agents that successfully target receptors or biological activities within the central nervous system have not been described. Attempts to design Tc-99m labeled chrysamine G (CG) and Congo Red (CR) derivatives or mixed functionalities such as isonitriles have been unsuccessful (Dezutter et al., 1999a; Dezutter et al., 1999b; Han et al., 1996). Despite having neutral $[Tc^vO]^{3+}N_2S_2$ cores, high conjugation, and high binding affinity, these agents are unable to permeate the intact blood-brain barrier.

Alzheimer's Disease

Recent estimates indicate that approximately 4 million Americans suffer from Alzheimer's disease (AD), a progressive neurodegenerative disorder with an estimated annual healthcare cost of $100 billion (Schumock, 1998). The clinical symptoms of AD include cognitive decline, irreversible loss of memory, disorientation, and language impairment (McKhann, 1984).

The AD brain is associated with loss of neurons in regions of the brain responsible for learning and memory (e.g., hippocampus) and involve the appearance of two distinct abnormal proteinaceous deposits: extracellular amyloid plaques, that are characteristic of AD, and intracellular neurofibrillary tangles (NFTs) that are found in other neurodegenerative disorders (McKhann, 1984; Weiner, 1997; Yanker, 1996). Amyloid plaques consist of dystrophic neurites, altered astrocytes, and microglia surrounding an insoluble fibrillar core comprised of amyloid β-proteins (Aβ). The family of amyloid β-proteins includes predominantly two variants: Aβ 40, which contains 40 amino acids, and Aβ 42 which is a form believed to be relatively more dangerous and which consists of 42 amino acids (Lansbury, 1996). Aβ is known to be derived from the ubiquitously expressed cell surface amyloid precursor protein (APP) (Games et. al., 1995; Hsiao et al., 1996; Teller, 1996).

Several lines of investigation suggest that overexpression of Aβ is an initiating event in the AD pathogenic cascade. Such evidence includes: a) overexpression of amyloid precursor protein (APP; a transmembrane protein encoded on chromosome 21) is characteristic of Down's Syndrome (DS) and early onset AD has been shown to be a virtual certainty in these patients (Lernere et. al., 1996b; Teller, 1996); b) missense mutations in APP are known as likely early triggers of AD; c) mutations in the presenilin proteins that may have a role in early onset AD have been shown to increase the expression of variant Aβ 42 (Lemere et. al., 1996a; Scheuner et. al., 1996; Selkoe, 1997); and d) transgenic mice that overexpress APP have been shown to develop AD-like neuropathology (Games et. al., 1995; Hsiao et al., 1996).

Currently, AD is diagnosed based on direct clinical observation of cognitive decline, coupled with the systematic elimination of other possible causes of those symptoms (McKhann, 1984; Weiner, 1997). No definitive premortem diagnostic procedure exists for AD, and while clinical observations suggest that amyloid formation precedes neurodegeneration, postmortem neuropathological examinations of amyloid plaques and neurofibrillary tangles (NFTs) typically provide the only direct evidence of the disease. Although the quantity of fibrillar amyloid roughly correlates with severity of symptoms at the time of death, the temporal relationship between amyloid deposition, neuronal loss, and cognitive decline is unclear.

Non-invasive AD Diagnostics

Certain non-invasive AD diagnostic probes are known, and hold some promise for enabling in vivo evaluation of the presence and/or extent of brain amyloid. Known non-invasive AD diagnostic probes include: a) Congo Red derivatized small organic molecules (Dezutter et al., 1999b; Klunk et al., 2002; Skovronsky et al., 2000); b) anti-Aβ monoclonal antibodies that bind specific amino acid residues of Aβ1-42/43 (Majocha et al., 1992; Walker et al., 1994); c) Aβ1-40 peptide derivatized with putrescine for increased permeability across the BBB, with appended chelation cores holding gadolinium (Gd-DTPA) or monocrystalline iron oxide nanoparticles (MION) (see, e.g. Weissleder et al., 2000); and d) iodine-123/125 and carbon-11 labeled thioflavin-based organic compounds that have been developed for in vivo labeling of Aβ plaques (Klunk et al., 2001; Kung et al., 2002).

However, these known imaging agents bear significant limitations. The Congo Red derivatized compounds are neutral, small molecular weight compounds which can permeate the blood-brain barrier, and can provide localization of an Aβ-targeted probe, but do not provide quantification capabilities. Anti-Aβ monoclonal antibodies do not readily permeate the blood-brain barrier. Aβ1-40 derivatized peptides bind or associate with plaques, and carry promise for detection of plaques through MRI, but such molecules do not readily permeate the blood brain barrier and require assistance from mannitol administration to induce permeation (Wadghiri et al., 2003). Such a procedure is unlikely to be approved for routine diagnostic use. Putrescine derivatized Aβ shows some permeability (Poduslo et al., 2002), but labeling with iodine-125 is susceptible to metabolism through deiodination reactions. Further, Aβ itself is known to be toxic (Kowall et al., 1992). Still further, studies using $^3$H-Aβ 1-40 with RBE4 cell monolayers (as a model of BBB permeability) in transwell experiments also indicate that Aβ1-40 is not transported across the monolayer. Finally, iodine-123/125 and carbon-11 labeled thioflavin-based organic compounds are promising, but agents labeled with iodine are prone to de-iodination reactions due to lability of the carbon-iodine bond when exposed to stringent in vivo environments over time. Carbon-11 agents hold some promise, but their extremely short half-life (20.4 minutes) restricts their accessibility to serve as efficient screening tools to those clinics associated with cyclotrons.

Thus, known non-invasive imaging tools as they apply to in vivo diagnosis of AD are currently quite limited for a variety of reasons. A clear need remains for tools and methods enabling premortem diagnosis of AD, elucidation of the pathogenesis of AD, and efficient monitoring of patients undergoing anti-amyloid therapeutic treatment. In particular, a need exists for non-invasive imaging techniques for visualizing AD-associated changes in the brain.

SUMMARY OF THE INVENTION

Accordingly, it is an object of the invention to overcome these and other problems associated with the related art. The present inventors have discovered blood-brain barrier (BBB) permeant peptides, and have demonstrated that such BBB permeant peptides can be used to selectively deliver nonpermeant or poorly permeant substances such as drugs, metals useful in medical therapy, imaging, and/or diagnostics, and diagnostic substances such as oligonucleotides, peptides, peptide nucleic acids, fluorochromes, dyes, enzyme substrates, to the central nervous system in vivo. The inventors have also succeeded in developing methods for coupling these substances to peptides for use in such methods. These and other objects, features and technical advantages are achieved by a BBB permeant, amyloid-targeting peptide coupled to a chelation core that can accommodate technetium-99m or other labels.

An exemplary BBB permeant, amyloid-targeting peptide comprises a purified peptide, the amino acid sequence of which comprises KKLVFFAeKGC (SEQ. ID. NO.: 1).

In another embodiment, the present invention provides a compound comprising a BBB-permeant, Aβ-targeting peptide coupled to a chelation core. For example, the compound comprises a peptide having the amino acid sequence of SEQ. ID. NO.: 1 coupled to a chelation core. The chelation core accommodates, for example, a medical imaging agent such as a radionuclide. Exemplary radionuclides include, without limitation, technetium-99m, technetium 94m and rhenium.

In an exemplary embodiment, the chelation core has the structure of Formula I:

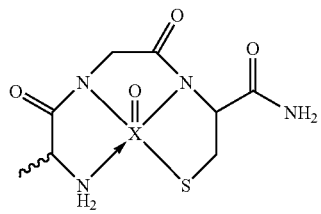

wherein X is selected from the group consisting of technetium-99m, technetium 94m and rhenium.

Other chemical structures are suitable for use as the chelation core. For example, in another embodiment of the compound, the chelation core has a structure selected from the group consisting of:

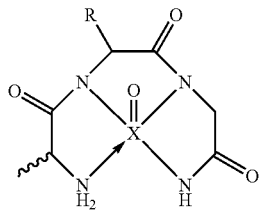

R = OH, COOH, (CH$_2$)$_4$NH$_2$

Formula I, wherein X is one of technetium-99m, technetium 94m and rhenium;

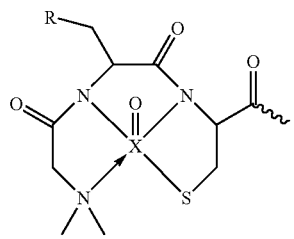

R = OH, COOH, (CH$_2$)$_3$NH$_2$

Formula II, wherein X is one of technetium-99m, technetium 94m and rhenium;

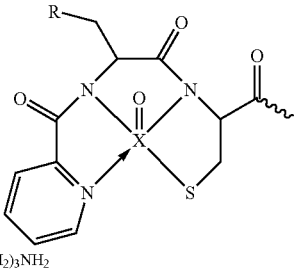

R = OH, COOH, (CH$_2$)$_3$NH$_2$

Formula III, wherein X is one of technetium-99m, technetium 94m and rhenium; and

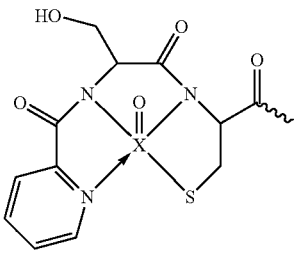

Formula IV, wherein X is one of technetium-99m, technetium-94m.

In another embodiment, the present invention provides a diagnostic compound for imaging amyloid deposits that includes a BBB permeant peptide, the amino acid sequence of which comprises SEQ. ID. NO.: 1, coupled to a chelation core to which is coupled a medical imaging agent, and a pharmaceutically acceptable excipient or diluent. The medical imaging agent is, for example, a radionuclide such as technetium-99m or technetium-94m.

In another embodiment, the present invention provides a method of detecting amyloid plaques in a living mammal, the method comprising providing a medical imaging agent coupled to a BBB permeant amyloid-targeting peptide. In one embodiment of the method, providing a BBB permeant amyloid-targeting peptide comprises synthesizing a peptide, the amino acid sequence of which comprises SEQ. ID. NO. 1. The method, in one embodiment, further comprises coupling a chelation core to the BBB permeant amyloid-targeting peptide. In another aspect, the method further includes coupling a chelation core to the BBB permeant amyloid-targeting peptide, wherein a medical imaging agent such as, for example, a radionuclide. In one embodiment, the medical imaging agent is technetium-99m. In another embodiment of the method, the medical imaging agent is technetium-94m.

In another embodiment, the present invention provides a method of constructing a BBB permeant amyloid-targeting peptide labeled with a medical imaging agent, the method comprising synthesizing a BBB permeant amyloid-targeting peptide, the amino acid sequence of which comprises SEQ. ID. NO.: 1, and coupling the peptide to a chelation core. In one embodiment, the method further comprises coupling a medical imaging agent to the chelation core. In one embodiment of the method, the medical imaging agent is technetium-99m. In another embodiment of the method, the medical imaging agent is technetium-94m.

In another embodiment of the method of constructing a BBB permeant amyloid-targeting peptide labeled with a medical imaging agent, DOTA (1,4,7,10-tetraazacyclododecane-1,4,7,10-tetraacetic acid) is used as the chelation core. The method comprises coupling DOTA to the BBB permeant amyloid-targeting peptide. A metal which acts as a medical imaging agent, such as copper-64 or gallium-68, is then coupled to the DOTA. Such a BBB permeant amyloid-targeting peptide can also be labeled with a fluorophore as the medical imaging agent. Suitable fluorophores include Congo-red based hydrophobic molecules such as, for example, X-34 or methoxy-X-04. Other suitable fluorophores include Fluorescein maleimide (FM), FITC (fluorescein-5-isothiocyanate) and Alexa Fluor 680.

In yet another embodiment, the present invention provides a method of screening for a BBB permeant amyloid-targeting peptide, the method comprising: generating a small peptide library comprising a plurality of peptides wherein each peptide has a distinct amino acid sequence, each such sequence comprising a partial sequence from Aβ40, the entire amino acid sequence of which is DAEFRHDSGYEVHHQKLVF-FAEDVGSNKGAIIGLMVGGVV (SEQ. ID. NO.: 2); testing each small peptide for amyloid-targeting specificity and BBB permeability; and comparing the amyloid-targeting specificity and BBB permeability of each small peptide to the amyloid-targeting specificity and membrane permeability of the peptide, the amino acid sequence of which comprises SEQ. ID. NO.: 1.

In yet another embodiment, the present invention provides a method of imaging amyloid deposits in a mammal, said method comprising introducing into the mammal a detectable quantity of a diagnostic composition for imaging amyloid deposits, the diagnostic composition including a BBB permeant amyloid-targeting peptide having the amino acid sequence of SEQ. ID. NO.: 1 coupled to a chelation core coupled to a medical imaging agent, and a pharmaceutically acceptable excipient or diluent, allowing sufficient time for the diagnostic composition to become associated with amyloid deposits; and detecting the labeled compound associated with one or more amyloid deposits.

In yet another embodiment, the present invention provides a method of delivering drugs to amyloid deposits in the brain of a subject, the method comprising introducing into the mammal a peptide conjugate comprising BBB permeant amyloid targeting peptide having the acid sequence of SEQ. ID. NO.: 1 coupled to a chelation core coupled to a pharmaceutically active substance, and allowing sufficient time for the peptide conjugate to become associated with one or more amyloid deposits, thereby delivering the compound to the amyloid deposits.

These and other features, aspects and advantages of the present invention will become better understood with reference to the following description, examples and appended claims.

BRIEF DESCRIPTION OF THE DRAWINGS

FIG. 1a is a structural drawing of an exemplary amyloid-targeting $^{99m}$Tc-peptide.

FIG. 1b is a chemical structure drawing of a resin-bound protected amyloid-targeting $^{99m}$Tc-peptide;

DETAILED DESCRIPTION OF THE PREFERRED EMBODIMENTS

Abbreviations and Definitions

Figure 3:
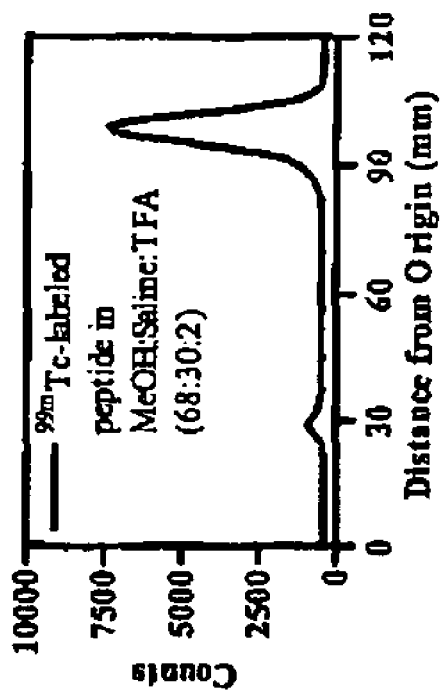
FIG. 3 is a graph of results from a radio-TLC analysis indicating stability of the $^{99m}$Tc-labeled peptide in human serum at 37° C. for 3 hours.

To facilitate understanding of the invention, a number of terms and abbreviations as used herein are defined below as follows:

Amino Acid: As used herein, the term "amino acid" is broadly defined to include naturally occurring amino acids as well as non-naturally occurring amino acids, including amino acid analogs and derivatives, such as molecules containing an amino acid moiety. As used herein, the term amino acid therefore embraces, for example, naturally occurring proteogenic L-amino acids; D-amino acids; chemically modified amino acids such as amino acid analogs and derivatives; naturally occurring non-proteogenic amino acids such as nor-leucine, β-alanine, ornithine, etc.; and chemically synthesized compounds having properties known in the art to be characteristic of amino acids, including non-native β-amino acids, those containing non-natural side chains, and D-amino acids as well as inverso and retro-inverso peptide sequences.

Amyloid: As used interchangeably herein, the terms "amyloid" and "Aβ" are broadly defined to include the family of proteins derived from the ubiquitously expressed cell surface amyloid precursor protein (APP), and that primarily form the brain fibrils which are a signal event in the pathogenesis of Alzheimer's disease. The amyloid family of proteins is known collectively as the amyloid β-proteins (Aβ), including predominantly two variants: Aβ 40 which has 40 amino acids, and Aβ 42 which has 42 amino acids.

Aβ 1-40: As used herein, the term "Aβ 1-40" refers to that sequence of forty (40) amino acids in common among all members of the amyloid protein family, which is the sequence of SEQ. ID. NO: 2.

Aβ-targeting: As used interchangeably herein, the terms "amyloid-targeting" and "Aβ-targeting" refer to a characteristic ability of a peptide to bind in specific, receptor-like fashion to Aβ 1-40, Aβ 1-42 and related Aβ fibrils. Binding assays as well known in the art are used to quantify specific binding abilities of a peptide by determining an affinity constant.

Blood-brain barrier: As used herein, the term "blood-brain barrier" or "BBB" refers to that obstacle to biological transport of drugs, ions, peptides, proteins and toxins that is formed by the membrane properties, structure and tight junctions of brain capillary endothelial cells.

Chelate: As used herein, the term "chelate" refers to an action of a chemical compound having a ring structure whereby the compound holds a free metal ion within the ring structure by forming bonds with the free metal ion.

Chelation core: As used herein, the term "chelation core" refers to a peptide structure or more generally an organic chemical structure that is capable of coupling to another peptide structure, and further characterized by structure that is capable of bonding with free metal ions, including medical imaging isotopes, such as technetium-99m, technetium-94m, indium-111, gallium-67, gallium-68 and copper-64 as well as paramagnetic metals, such as gadolinium.

Conjugate: As used herein in combination with the term "peptide", the term "conjugate" refers to the product formed by coupling a peptide with one or more other moieties or chemical groups, such as a chelation core.

Coupled: As used herein the term "coupled" broadly refers to a characteristic of a first chemical constituent with respect to a second chemical constituent, wherein a chemical bond is formed between the two constituents, such as between an organic molecule acting as a chelation core and a peptide or peptide fragment, and also as between a chelation core and a metal ion.

Fragment: As used herein with respect to peptide, the term "fragment" is broadly defined to include any partial or incomplete amino acid sequence taken from a longer complete amino acid sequence coding for a peptide.

Functional linker moiety: As used herein, the term "functional linker moiety" refers to an amino acid sequence that serves as a coupling sequence between two other amino acid sequences, and is further capable of being disrupted by an enzyme such as a protease such that the reaction of the enzyme with the functional linker moiety causes the two other previously coupled amino acid sequences to uncouple.

Labeled: As used herein with respect to a BBB permeant Aβ-targeted peptide, the term "labeled" refers to the characteristic of including in its chemical structure a ligand that provides a signal that enables monitoring of the behavior of the peptide in vitro and in vivo. The term "radiolabeled" as used herein with respect to a BBB permeant Aβ-targeted peptide refers to the characteristic of including in its chemical structure a radioligand that provides a radioactivity signal for monitoring the behavior of the peptide in vitro and in vivo.

Medical imaging agent: As used herein, the term "medical imaging agent" refers to an ion, molecule, compound or composition of matter that, when administered to a living subject such as a mammal, acts as an instrument for visualizing internal structures and function of the subject.

Membrane: As used herein, the term "membrane" refers to the external lipid bilayer of an animal cell that separates the interior of the cell from its exterior environment including other cells.

Metal chelation ligand: As used herein, the term "metal chelation ligand" refers to metals useful for chelation into the peptide conjugates of the present invention, including radioactive metals (radionuclides) having decay properties that are amenable for use as a diagnostic tracer or for deposition of medically useful radiation within cells or tissues. Such radionuclides include, without limitation, radioactive isotopes of Tc, Ru, In, Ga, Co, Pt, Fe, Os, Ir, W, Re, Cr, Mo, Mn, Ni, Rh, Pd, Nb, Cu and Ta, for example, Tc-99m, Tc-99, Tc-94m, In-111, Ga-67, Ga-68, Cu-64, Ru-97, Cr-51, Co-57, Re-188, and Re-186. Other radionuclides embraced by the term "metal chelation ligand" include, without limitation, I-123, I-125, I-130, I-131, I-133, Sc47, As-72, Se-72, Y-90, Y-88, Pd-100, Rh-100m, Sb-119, Ba-128, Hg-197, At-211, Bi-212, Pd-212, Pd-109, Cu-67, Br-75, Br-76, Br-77, C-11, N-13, O-15, F-18, Pb-203, Pb-212, Bi-212, Cu-64, Ru-97, Rh-105, Au-198, and Ag-199. The term "metal chelation ligand" also embraces relaxivity metals including, but not limited to, Mn, Cr, Fe, Gd, Eu, Dy, Ho, Cu, Co, Ni, Sm, Tb, Er, Tm, and Yb.

Motif: As used herein the term "motif" refers to a pattern in a sequence of nucleotides or amino acids, or to a pattern of chemical features in an organic molecule, wherein the pattern is associated with certain functional characteristics of the molecule.

Peptide: As used herein, the term "peptide" is broadly defined to include any organic compound consisting of two or more amino acids joined by a chemical bond in which the amino group of one amino acid combines with the carboxyl group of a second amino acid.

Permeant: As used herein, the term "permeant" refers to that characteristic ability of a molecule, especially a bioactive molecule, to penetrate a barrier, such as a cell membrane or particularly the blood brain barrier formed by brain capillary endothelial cells.

Pharmacologically active: As used herein, the term "pharmacologically active" broadly refers to that characteristic of a compound or composition which confers the ability of the compound or composition to have an effect on physiologic function when administered to an animal subject.

Proteogenic: As used herein, the term "proteogenic" refers to that characteristic of an amino acid which enables the amino acid to be incorporated into a peptide, polypeptide, or protein in a cell through a metabolic pathway.

Reducing agent: As used herein, the term "reducing agent" refers to a chemical compound used to reduce another chemical compound by donating electrons, thereby becoming oxidized.

Small peptide: As used herein, the term "small peptide" refers to a peptide consisting of from three to twenty amino acids, and in a preferred embodiment from three to ten amino acids, and in a most preferred embodiment from four to nine amino acids.

BBB Permeant Aβ-targeted Peptides

The definitive diagnosis of Alzheimer's disease (AD) relies on detection of amyloid plaques, which until now has not been achieved in living patients but only in postmortem brain. Methods for interrogating the efficacy of new therapies in AD while patients are undergoing therapy have also been limited by the inability to monitor amyloid plaques in living patients. Thus, a noninvasive method to diagnose AD by detecting amyloid plaques in living patients will greatly advance the diagnosis and management of AD.

Candidate Aβ-targeted imaging agents ideally possess four critical characteristics: a) specific binding to Aβ plaques; b) permeability across the blood-brain barrier; c) metabolic stability; and d) efficient synthesis for rapid formulation. The compositions and related methods of their use according to the present invention provide these and more advantages.

Briefly, the novel peptide conjugates of the current invention include: an Aβ-targeting region which is also BBB permeant, and a chelation core. A functional linker moiety as described below is optionally included. The Aβ-targeting region of the peptide conjugates is a novel purified peptide which, in an exemplary embodiment, has the amino acid sequence KKLVFFAεKGC (SEQ. ID. NO.: 1). Transwell transport studies that a peptide conjugate including the purified peptide coupled to a chelation core to which technetium-99m ($t_{1/2}$=6 h; 140 KeV) has been coupled, demonstrates both amyloid-targeting ability and the surprising and unexpected ability to transport across cell membranes, indicating the ability to penetrate the blood-brain barrier.

Thus, the inventors have succeeded in synthesizing and characterizing novel, non-metabolized, BBB permeant Aβ-targeted peptides and peptide conjugates that enable medical imaging of amyloid deposits. The inventors have further characterized novel peptide conjugates using the structure-activity relationships (SAR) of the Aβ-targeted region and the chelation core and the optionally included linker moiety. Novel is the coupling of a chelation core, specifically a chelation core that chelates radioactive metals or other metals of interest for imaging (e.g., magnetic resonance relaxivity metals) or radiotherapy, to a BBB-permeant peptide to produce a BBB-permeant, amyloid-targeting peptide conjugate capable of delivering a medical imaging agent. Also novel is the optional use of a functional linker moiety as a coupling agent between the BBB-permeant peptide and a chelation core, whereby the characteristic susceptibility of the functional linker moiety to degradation by a cellular enzyme such as a protease enables selective delivery of the chelation core, including a metal ligand, across the BBB and retention of the chelation core including metal ligand in brain tissue. Such BBB permeant peptides and peptide conjugates provide the following benefits: biological efficacy (broadly defined as high uptake in the targeted site, high target-to-background ratio, high target specificity/sensitivity, quick formulation in a radio-pharmacy; and suitability for kit-formulation for wide delivery and application.

Thus, in one embodiment, the present invention provides a compound comprising a BBB-permeant, Aβ-targeting peptide coupled to a chelation core. The chelation core is chemical ring structure which is both capable of coupling to the peptide and capable of bonding with free metal ions, such as the isotopes which function as medical imaging agents and which are particularly useful in the compounds and methods of the present invention. The chelation core is capable of bonding, for example, such medical imaging agents as technetium-99m, technetium-94m, rhenium, indium-111, gallium-67, gallium-68 and copper-64, as well as paramagnetic metals, such as gadolinium.

For example, in one embodiment, the chelation core has the structure of Formula I,

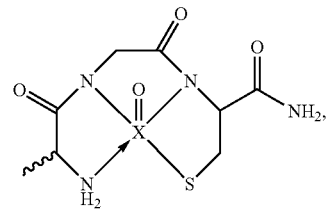

wherein X is one of technetium-99m, technetium-94m, and rhenium.

Alternative chelation cores are suitable for use in the peptide conjugates of the present invention. For example, in one embodiment, a peptide conjugate includes a BBB-permeant, Aβ-targeting peptide such as a peptide having the amino acid sequence of SEQ. ID. NO.: 1, the peptide coupled to a chelation core selected from the group consisting of:

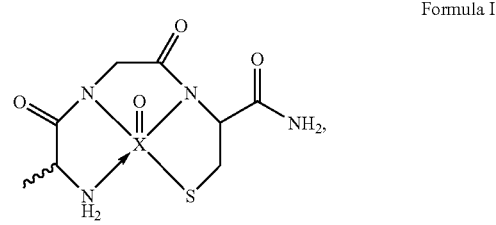

Formula I

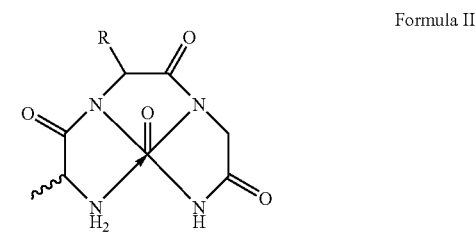

Formula II

R = OH, COOH, $(CH_2)_4NH_2$,

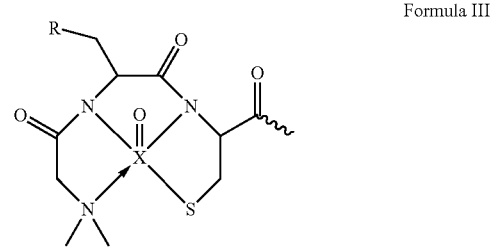

Formula III

R = OH, COOH, $(CH_2)_3NH_2$; and

-continued

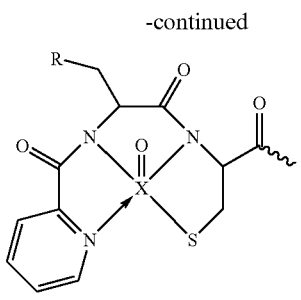

Formula IV

R = OH, COOH, (CH$_2$)$_3$NH$_2$, wherein X is one of technetium-99m, technetium-94m and rhenium.

Peptides and peptide conjugates in accordance with the present invention can be readily prepared by automated solid phase peptide synthesis (SPPS)(Houghten, 1985; Lin et al., 1988; Merrifield et al., 1982) using any one of a number of well known, commercially available automated synthesizers, such as Applied Biosystems ABI 433A peptide synthesizer. Many combinations of natural and non-natural amino acids and peptide sequence mimetics (peptidomimetics) are possible, and selective engineering of favorable target-binding and pharmacokinetic properties can be accomplished with natural and unnatural peptides (Lister-James et al., 1997a). Peptidomimetics are unnatural biopolymers that do not contain alpha-amino acids, but rather incorporate backbone structures with hydrogen-bonding groups (such as urea), chiral centers, side chain functionalities, and a sufficient degree of conformational restriction to behave similar to, or mimic the bioactivities of, a natural polypeptide.

To prepare a peptide that is both BBB permeant and Aβ-targeted, the amino acid sequence of which comprises, for example, KKLVFFAϵKGC (SEQ. ID. NO.: 1), the amino acids are coupled using SPPS using L- or D-N-α-FMOC-protected amino acid residues and standard coupling techniques as well known in the art. Similarly, the chelation core is coupled via its amino acid side chain directly to the BBB permeant Aβ-targeted peptide. Alternatively, a functional linker moiety as described below is an intervening amino acid sequence which is coupled using SPPS to both the BBB permeant and Aβ-targeted peptide and the chelation core. The resulting peptides and peptide conjugates are purified, for example, using analytical HPLC technique. Principles and protocols for peptide synthesis in general are described, for example, in (Pennington and Dunn, 1994).

Principles and protocols more specifically relating to SPPS are described in (Grant, 2002) and (Chan and White, 2002), respectively. SPPS involves attaching a first protected amino acid to an insoluble polystyrene solid support via an acid labile linker. The amino acids are protected, for example, by a temporary acid labile protecting group, such as t-butoxycarbonyl (t-Boc), on the α-amino position, and by a more acid stable benzyl type protecting group on the functionality of the side chain. The t-Boc group is deprotected by trifluoroacetic acid (TFA) followed by the neutralization and washing steps, and then the next protected amino acid couples to the amino peptide resin in the presence of activator. Alternatively, the first amino acid is protected by a temporary base labile α-amino protecting group, 9-fluorenylmethoxycarbonyl (Fmoc). Generally speaking in Fmoc SPPS, the α-amino group is protected by Fmoc and the side chain functionality is protected by the acid labile t-butyl type protecting groups. Fmoc-based SPPS offers the advantage of a milder acid cleavage process. In either case, the deprotection and coupling steps are repeated to add each amino acid in the sequence until the desired sequence of the peptide is assembled. The final peptide is cleaved and deprotected from the resin simultaneously by liquid hydrogen fluoride in a specialized apparatus. Fmoc SPPS has been used successfully to synthesize many long peptides in the range of at least 100 and more amino acid residues, including human parathyroid hormone (84 residues), HIV-1 aspartyl protease (99 residues) and interleukin-3 (140 residues). Accordingly, Fmoc SPPS is more than well-suited to synthesize the relatively short peptides (10 residues) of the present invention.

In general, SPPS requires a well-solvated gel to allow the reactions to take place between the reagents in the mobile phase and the functional groups on chains throughout the surface of a resin. Suitable resins include a polystyrene polymer cross-linked with 1% of 1,3-divinylbenzene, having a swelling capacity 3-fold in volume in DMF. Another suitable, more recently developed resin is a polyamide resin introduced by Atherton and Sheppard (Atherton and Sheppard, 1989) wherein the solid support and peptide backbone are of comparable polarities. Other resins have been developed that are based on grafting of polyethylene glycol (PEG) to low cross-linked polystyrene. Such resins include, for example, Tentagel (Bayer and Rapp, 1986) and PEG-PS resins (Barany et al., 1992) with a swelling capacity 5-fold in volume in DMF. More recently, resins such as PEGA (Meldal, 1992) and CLERA resins (Kempe and Barany, 1996), with a swelling capacity of 11- and 6.5-fold in volume, respectively, and which are based on cross-linked PEG have also been made available.

In SPPS, the linker provides a reversible linkage between the peptide chain and the solid support, and protects the C-terminal α-carboxyl group. The most commonly used resins to provide peptide acids are Wang, Hydroxymethyl-phenoxy acetyl (HMPA), Rink acid, 2-Chlorotrityl chloride, and SASRIN. The most commonly used resin for peptide amides is Rink amide resin.

Esterification of the first amino acid to the hydroxyl group on the resin is an important step in building a robust peptide. Incomplete loading and racemization causes truncated and epimeric peptides respectively, a result of a slow esterification reaction. The most commonly used loading methods are the HOBt active ester, symmetrical anhydride and dichlorobenzoyl chloride procedures. The first amino acid residue can be loaded to trityl-based resins with no racemization. For routine synthesis, the global protecting strategy is employed to all reactive functionalities of the side chains. For instance, hydroxyl and carboxyl functionalities are protected by t-butyl group, lysine and tryptophan are protected by t-Boc group, and asparagines, glutamine, cysteine and histidine are protected by trityl group, and arginine is protected by the pbf (2,2,4,6,7-pentamethyldihydrobenzofuran-5-sulfonyl) group. A wide range of protecting groups are also available for different applications such as Hmb (2-hydroxy-4-methoxybenzyl) group used as an amide protecting group to alleviate aggregation during SPPS. Fmoc deprotection is typically accomplished by treatment with, for example, 20-50% piperidine in DMF, for a period of about 20 minutes. In the case of incomplete Fmoc deprotection, a stronger base such as 1,8-diazabicyclo[5.4.0]undec-7-ene (DBU) with 2% piperidine can be used.

Amide bond formation involves activation of the carboxyl group of the amino acid. There are four major coupling techniques: (a) in situ coupling reagents such as carbodiimide-mediated coupling, BOP, HBTU as well as HATU, (b) preformed active esters such as Opfp, Osu, Onp, (c) preformed symmetrical anhydrides, (d) acid Halides such as acyl fluoride as well as acyl chloride.

The reiterative process, and especially completion of deprotection and coupling, is typically monitored to ensure the success of the SPPS. Typically, the Ninhydrin test is used to examine the presence of free amino groups which are a result of incomplete coupling. However, other methods such as the TNBS and the Chloranil test can be used as alternative or complementary methods to the Ninhydin test.

Fmoc SPPS is designed for simultaneous cleavage of the anchoring linkage and global deprotection of side-chain-protecting groups with TFA. The most commonly used cleavage cocktail is Reagent K (TFA/thioanisol/water/phenol/EDT: 82.5:5:5:5:2.5 v/v).

Analytical HPLC is now routinely used to determine the purity of peptide, together with mass spectral analysis to determine the peptide identity. Most crude peptides can be purified alone by reversed phase HPLC to achieve the desired purity. In the case of crude peptides of inferior quality, combinations of anion or cation HPLC purification followed by reversed phase HPLC purification comprise a powerful approach for purifying crude peptide. Data from sequence analysis and amino acid analysis can provide further detailed information on peptide homogeneity.

By using an orthogonal protecting group strategy ("orthogonal approach"), resins with novel linkers, and customized cleavage protocols, modified peptides are now routinely synthesized. Such modified peptides include, but not limited to, biotinylated, branched, chromogenic, C-terminal modified, fatty acid containing, fluorescent, glycosylated, isoprenated, cyclic lactam multiple disulfide, peptide mimetics, phosphorated and sulfation peptides.

The incorporation of non-naturally occurring amino acids, including synthetic non-native amino acids, substituted amino acids, one or more D-amino acids, or synthetic amino acid sequences into the peptides, or in the chelation core or functional linker moieties of the present invention is advantageous in a number of different ways. D-amino acid-containing peptides (hereinafter referred to as "D-peptides") exhibit increased stability in vitro or in vivo compared to L-amino acid-containing counterparts. Thus, the construction of peptides incorporating D-amino acids can be particularly useful when greater stability is desired or required. More specifically, D-peptides are resistant to endogenous peptidases and proteases, thereby providing improved bioavailability of BBB-permeant conjugates, and prolonged intravascular and interstitial lifetimes when such properties are desirable. The use of D-peptides can also enhance BBB delivery of linked drugs and other cargo molecules. Additionally, D-peptides cannot be processed efficiently for major histocompatibility complex class 11-restricted presentation to T helper cells, and are therefore less likely to induce humoral immune responses in the whole organism. Peptides and peptide conjugates can therefore be constructed using, for example, D-peptide BBB permeant sequences, functional L-peptide linker moieties, and D-peptide chelation sequences. In this embodiment, only the functional L-peptide linker moiety would be able to interact with native enzymatic activities such as proteases, kinases, and phosphatases, thereby providing enhanced selectivity, prolonged biological half-life, and improved signal-to-noise ratio for selected imaging applications. On the other hand, when it is more desirable to allow the peptide to remain active for only a short period of time, the use of L-amino acids in the peptide can allow endogenous peptidases in a cell or organism to digest the peptide in vivo, thereby limiting exposure to the BBB-permeant peptide conjugates comprising the peptides disclosed herein.

The peptide conjugates can be optionally constructed using a functional linker moiety containing an amino acid sequence which is particularly or specifically susceptible to degradation by a cellular enzyme such as a protease. Susceptibility to protease degradation is advantageous for the delivery of compounds to targets beyond the BBB. For example, a peptide conjugate can be constructed using a functional linker moiety containing an amino acid sequence that is susceptible to degradation by the enzyme cadhepsin D. Such a peptide conjugate would be particularly useful for delivering compounds including therapeutic or diagnostic agents to the cancer cells in which cadhepsin D is selectively active.

In addition to using D-amino acids, those of ordinary skill in the art are aware that modifications in the amino acid sequence of a peptide, polypeptide, or protein can result in equivalent, or possibly improved, second generation peptides, etc., that display equivalent or superior functional characteristics when compared to the original amino acid sequence. The present invention accordingly encompasses such modified amino acid sequences. Alterations can include amino acid insertions, deletions, substitutions, truncations, fusions, shuffling of subunit sequences, and the like, provided that the peptide sequences produced by such modifications have substantially the same functional properties as the naturally occurring counterpart sequences disclosed herein. Thus, for example, modified BBB-permeant peptides should possess substantially the same BBB translocation and delivery properties as the naturally occurring counterpart sequence.

One factor that can be considered in making such changes is the hydropathic index of amino acids. The importance of the hydropathic amino acid index in conferring interactive biological function on a protein has been discussed by Kyte and Doolittle (Kyte and Doolittle, 1982). It is accepted that the relative hydropathic character of amino acids contributes to the secondary structure of the resultant polypeptide. This, in turn, affects the interaction of the polypeptide with molecules such as enzymes, substrates, receptors, DNA, antibodies, antigens, etc.

Based on its hydrophobicity and charge characteristics, each amino acid has been assigned a hydropathic index as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

As is known in the art, certain amino acids in a peptide or protein can be substituted for other amino acids having a similar hydropathic index or score and produce a resultant peptide or protein having similar biological activity, i.e., which still retains biological functionality. In making such changes, it is preferable that amino acids having hydropathic indices within +/−2 are substituted for one another. More preferred substitutions are those wherein the amino acids have hydropathic indices within +/−1. Most preferred substitutions are those wherein the amino acids have hydropathic indices within +/−0.5.

Like amino acids can also be substituted on the basis of hydrophilicity. U.S. Pat. No. 4,554,101 discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0.+−0.1); serine (+0.3); asparagine/glutamine (+0.2); glycine (0);

threonine (−0.4); proline (−0.5.+−0.1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4). Thus, one amino acid in a peptide, polypeptide, or protein can be substituted by another amino acid having a similar hydrophilicity score and still produce a resultant protein having similar biological activity, i.e., still retaining correct biological function. In making such changes, amino acids having hydropathic indices within +/−2 are preferably substituted for one another, those within +/−1 are more preferred, and those within +/−0.5 are most preferred.

As outlined above, amino acid substitutions in the peptides of the present invention can be based on the relative similarity of the amino acid side-chain substituents, for example, their hydrophobicity, hydrophilicity, charge, size, etc. Exemplary substitutions that take various foregoing characteristics into consideration in order to produce conservative amino acid changes resulting in silent changes within the present peptides, etc., can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral non-polar amino acids such as alanine, leucine, isoleucine, valine, proline, phenylalanine, tryptophan, and methionine. It should be noted that changes that are not expected to be advantageous can also be useful if these result in the production of functional sequences. Since small peptides can be easily produced by conventional solid phase synthetic techniques, the present invention includes peptides, linker moieties, and conjugated molecules such as those discussed herein, containing the amino acid modifications discussed above, alone or in various combinations. To the extent that such modifications can be made while substantially retaining the BBB permeability and targeting properties of the peptide, and the biological function and specificity of the linker moiety and conjugated chelation cores, drugs and cargo moieties, they are included within the scope of the present invention. The utility of such modified peptides, linkers, and cargos can be readily determined by, for example, the methods described in the examples below.

The metallic character of Tc-99m and other useful metal ions requires that it be stabilized by the chelation core to be coupled to the peptide. This chelation core may typically involve a multiple heteroatom coordination system, or the formation of a non-labile organometallic species. There are two broad strategies for binding metals for biological applications. These are "the pendant approach" and "the integrated approach," which have been reviewed by Katzenellenbogen and colleagues (Hom and Katzenellenbogen, 1997). The pendant (or conjugate) approach involves the strategic placement of a Tc-99m-chelator-tether moiety at a site on the ligand that will not hinder binding of the ligand to its high affinity receptor. The integrated approach replaces a component of a known high-affinity receptor ligand with the requisite Tc-99m chelator such that there is a minimal change in the size, shape, structure, and binding affinity of the resultant molecule. Applications involving peptide-based imaging agents typically use the conjugate design, whereby an appropriate metal chelating moiety is affixed to the amino or carboxy terminus of the targeting peptide. In the present invention, the chelation cores are coupled to the peptide using SPPS and the pendent approach.

Preparation of Labeled Peptide Conjugates

Labeled peptide conjugates including a metal in the chelation core functioning as a medical imaging agent can be readily prepared by methods known in the art. For example, a BBB-permeant amyloid-targeting peptide conjugate can be admixed with a salt of a radioactive metal in the presence of a suitable reducing agent, if required, in aqueous media at temperatures from room temperature to reflux temperature, and the end-product peptide conjugate can be obtained and isolated in high yield at both macro (carrier added, e.g., Tc-99) concentrations and at tracer (no carrier added, e.g., Tc-99m) concentrations (typically less than $10^{-6}$ molar). It is well established that when (Tc-99m)pertechnetate ($TcO_4^-$) is reduced by a reducing agent, such as stannous chloride, in the presence of chelating ligands such as, but not restricted to, those containing $N_2S_2$, $N_2SO$, $N_3S$ and $NS_3$ moieties, complexes of $(TcO)N_2S_2$, $(TcO)N_2SO$, $(TcO)N_3S$ and $(TcO)NS_3$ are formed (Meegalla et al. 1997). Another preferred method for radiolabeling the peptide conjugate involves the use of glucoheptonate together with a reducing agent such as stannous chloride to label the chelation core on the peptide (Lister-James et al., 1996; Meegalla et al., 1997). Tc-99m chelation cores can be incorporated into potential receptor-selective imaging agents (Hom and Katzenellenbogen, 1997).

In one embodiment, the medical imaging agent is technetium-99m. Technetium-99m (Tc-99m; $t_{1/2}$=6 hours; 140 keV emission photon) is the most commonly used radionuclide in diagnostic nuclear medicine (Jurisson et al., 1993). It can be readily produced by molybdenum-99/technetium-99m generators available in clinical nuclear medicine radiopharmacy laboratories, and has favorable emission characteristics that enable ready detection with clinical gamma cameras. Moreover, the general availability of supplies of pertechnetate from a variety of commercial vendors makes it convenient to use kits for preparation of various Tc-99m peptide conjugates. In preferred embodiments of this invention, the peptide conjugate is radiolabeled with Tc-99m using standard reducing agents with or without transmetallation reactions (Grummon et al., 1995; Lister-James et al., 1996; Meegalla et al., 1997). For example, the peptide conjugate can be readily radiolabeled with technetium-99m in the chelation core through the ligand exchange procedure using $^{99m}$Tc-glucoheptonate and separating the desired fraction through radio-RP-HPLC. However, labeling of the peptide conjugates of the present invention with any radionuclide can be readily performed. For example, alternative embodiments are readily prepared in which technetium-94m or rhenium metal is exchanged for technetium-99m using standard ligand exchange procedures (Lister-James et al., 1997a; Lister-James et al., 1997b; Polyakov et al., 2000).

Radioactive and Non-Radioactive Metals

While the peptide conjugates of the present invention preferably contain Tc-99m and the closely related rhenium isotopes (Re-186 and Re-188), other metals, in addition to those already listed, are also useful in the present invention. Other metals useful as medical imaging agents in the peptide conjugates of the present invention include radionuclides having decay properties that are amenable for use as diagnostic tracers or for deposition of medically useful radiation within cells or tissues. The present invention consequently encompasses the use of peptide conjugates coupled to a radionuclide. The radionuclide can, for example, be selected from the group consisting of radioactive isotopes of Tc, Ru, In, Ga, Co, Pt, Fe, Os, Ir, W, Re, Cr, Mo, Mn, Ni, Rh, Pd, Nb, Cu and Ta, for example, Tc-99m, Tc-99, Tc-94m, In-111, Ga-67, Ga-68, Cu-64, Ru-97, Cr-51, Co-57, Re-188, and Re-186. Such peptide conjugates can be used for medical imaging and specifically for SPECT or PET imaging, as provided herein. Other metals useful for imaging and radiotherapy such as I-123, I-125, I-130, I-131, I-133, Sc47, As-72, Se-72, Y-90, Y-88, Pd-100, Rh-100m, Sb-119, Ba-128, Hg-197, At-211, Bi-212, Pd-212, Pd-109, Cu-67, Br-75, Br-76, Br-77, C-11, N-13, O-15, F-18, Pb-203, Pb-212, Bi-212, Cu-64, Ru-97, Rh-105, Au-198, and Ag-199 are also encompassed within the scope of this invention.

Non-radioactive metals useful for MR imaging can be incorporated into an appropriate chelation core useful for binding relaxivity metals which in turn has been coupled to the peptide conjugate as described above. Accordingly, useful metals also include isotopes of those metals possessing paramagnetism which produce water relaxation properties useful for generating images with magnetic resonance imaging (MRI) devices. Suitable relaxivity metals include, but are not limited to, Mn, Cr, Fe, Gd, Eu, Dy, Ho, Cu, Co, Ni, Sm, Tb, Er, Tm, and Yb. Appropriate chelation cores to bond MR relaxivity metals can be readily coupled to the peptides of this invention by the methods previously described for chelation cores for radionuclides. Such chelation cores for MT relaxivity metals include, but are not limited to, DTPA, EDTA, DOTA, TETA, EHPG, HBED, ENBPI, ENBPA, and other cross-bridge macrocycles known to those skilled in the art (Stark and Bradley, 1988).

A preferred embodiment of this invention is the coupling of DOTA (1,4,7,10-tetraazacyclododecane-1,4,7,10-tetraacetic acid) to the peptide using methods referenced above and using Gd as the MR relaxivity metal. Gd can be chelated into the DOTA moiety by reaction of chloride salts of Gd, such as $GdCl_3$, with the peptide chelate conjugate under mildly acidic conditions (pH 5-6) using standard techniques (Stark and Bradley, 1988; Wen-hong et al., 1999). DOTA can also serve as a platform for incorporating other medical imaging isotopes, such as copper-64 or gallium-68.

Alternatively, modifications to the BBB permeant amyloid-targeting peptide include coupling a fluorophore directly to the peptide. Suitable fluorophores include, for example, a Congo-Red based hydrophobic molecule such as X-34 or methoxy-X-04. Other suitable alternative fluorophores are FITC (fluorescein-5-isothiocyanate), fluorescein maleimide and Alexa Fluor 680 (available from Molecular Probes) for optical imaging. Moreover, the present invention also encompasses modified peptide conjugates in which both DOTA and a chelation core, or both a fluorophore and a chelation core are coupled to the peptide, as well as modified peptides in which DOTA and a fluorophore are coupled to the basic BBB permeant amyloid-targeting peptide. For example, modified peptide conjugates which include two rather than one single added moiety have a first moiety added to the N-terminus of the peptide, and the second moiety added to the C-terminus of the peptide. More specifically, for example, in one embodiment DOTA is coupled to the N-terminus of the peptide, and a fluorophore is coupled to the C-terminus.

Characterization of Peptide Conjugates

To confirm stability of the peptide conjugates in vivo, a radiolabeled peptide conjugate containing, for example, technetium-99m in the chelation core, is incubated in human serum at about 37° C. for several hours (e.g. 3-24 hours). Thereafter, radio-TLC analysis using a radiometric detection system such as a Bioscans 2000 is performed to evaluate the presence of metabolites in the mixture. Persistence of only the parental peptide conjugate indicates stable incorporation of the radio-metal within the chelation core of the sample peptide conjugate being tested.

Binding assays are performed to determine the binding specificity of the peptide conjugate. For example, a preliminary radioassay of Aβ-binding is performed. For example, a conjugate consisting of radiolabeled $^{99m}$Tc-peptide conjugate is incubated with Aβ fibrils in PBS for about 1-3 hours. Bound $^{99m}$Tc-peptide conjugate is separated on a Centricon filter unit (with, for example a 100 KDa cut off) and washed several times with PBS buffer. Saturable binding is indicated by calculation of a $K_d$ (affinity constant) as well known in the art to help evaluate the relative amount of specific binding as opposed to non-specific binding. Competitive binding of the peptide conjugate is demonstrated by incubating the bound peptide conjugate (bound to Aβ fibrils) with increasing concentrations of unlabeled peptide conjugate or, for example, cold Re-peptide conjugate. Radiolabeled peptide conjugate that is displaceable to background with either 1,000-fold molar excess of unlabeled peptide conjugate or, for example, cold Re-peptide conjugate, supports receptor-like binding behavior of the peptide conjugate to Aβ fibrils.

To demonstrate permeability across the BBB, immortalized rat brain endothelial cells (RBE4) are used in transwell transport experiments, having previously been established as a valid in vitro model of the BBB (Mroczkowsa et al., 2000). In brief, RBE4 cells are cultured to confluence on collagen filter inserts in a transwell configuration. For example, a radiolabeled peptide conjugate to be tested, such as $^{99m}$Tc-peptide conjugate, is added with a known BBB permeable compound (positive control) and a known non-permeant compound (negative control) to one chamber of a transwell apparatus containing RBE4 cell monolayers. Permeation of control and test compounds in the apical to basolateral direction, and in the basolateral to apical direction, is evaluated over a period of several minutes to several hours. An exemplary suitable period is about 120 minutes. For example, a macromolecular marker such as $^{14}$C-inulin is used as a negative control for monitoring paracellular leak pathways present in the cell monolayers (Violini et al., 2002), and confirming the presence of tight junctions and barrier formation with the RBE4 cells. A suitable compound for a positive control is a diffusible, hydrophobic compound, such as $^3$H-propranolol, to confirm the technique for determination of high transcellular permeation across the RBE4 cells. Amounts of positive and negative controls, and amount of peptide on each side of the monolayer are determined and used to quantify permeation of the peptide conjugate. Peptide conjugates in accordance with the present invention show robust permeation in such transwell configurations, even within a relatively brief period of about 120 minutes.

To demonstrate target specificity and permeability, biodistribution studies of radiolabeled peptide conjugate are performed, for example in normal mice. Comparison of the radiolabel signal in normal mice brain after several minutes (for example, 2-10 minutes) post tail-vein injection, are compared to the signal from a brain permeant dye such as 11C-methoxy-X34 (Klunk et al., 2002) over the same time period. Washout of the radiolabeled peptide conjugate signal over a subsequent period of about 30 minutes to 120 minutes is also attempted. Results from such in vivo studies complement the in vitro transwell data as indicators of permeation of the radiolabeled peptide conjugate across the BBB.

Staining experiments with cross sections of brain tissue from normal (WT) and APPsw+/− mice are suitable for evaluating target specificity of the peptide conjugate. For example, a candidate peptide conjugate is labeled with a fluorescent marker. A suitable marker is fluorescein-5-maleimide (FM; 3-equiv) in DMF, which labels the C-terminal thiol of the peptide. After a suitable reaction of peptide and FM at room temperature in the dark, the fluorescent-labeled peptide is purified, for example column-purified, requisite fraction eluted, combined, lyophilized and characterized through electron spray mass spectrometry. For tissue staining of brain sections of APPsw+/− mice (test) and WT mice (control), immunohistochemical staining of Aβ and for FM-peptide staining are performed according to published procedures (DeMattos et al., 2002; Holtzman et al., 2000). Rabbit-anti-pan Aβ antibody is used, for example, as a control, and visualized with anti-rabbit antibody conjugated with a fluorescent marker such as Alexa 568 (Molecular Probes). Staining of brain sections from normal and APPsw+/− mice are compared. Target specificity of the peptide is indicated by immunostaining of Aβ in APPsw+/− mice and no staining in WT mice. Similarly, using the Aβ-binding peptide coupled with FM, specific staining of plaques in the cortical region of brain sections in APPsw+/− mice is observed with target-specific peptide. In comparison, little or no staining is seen in WT mice, thus demonstrating the targeting specificity of the peptide.

Structure-activity relationships (SAR) are typically used to further characterize candidate bioactive molecules, and comparative SAR of related molecules is especially useful. SAR evaluations of BBB permeant Aβ-targeted peptide conjugates including a functional linker moiety involve maintaining unchanged the linker moiety, while the chelation core and/or the amyloid targeted peptide are varied and function in terms of BBB permeability and Aβ-targeting specificity are evaluated with each variant. For example, modifications subject to SAR evaluation would include D-inverso, retroinverso, and scrambled sequences (of the amyloid targeted region) to evaluate the impact of each change on targeting properties and/or permeation capability. In addition, the permeation motifs and chelation core can be swapped from N-terminus to C-terminus to evaluate any positional or steric preferences on Aβ-targeting properties. Because the coordination chemistry of technetium and rhenium are essentially similar (Liu and Edwards, 1999), if not commonly identical, peptide conjugates including the radioligand will be obtained through a ligand exchange method using technetium-99m- or cold rhenium-glucoheptonate. All peptides are purified by RP-HPLC, characterized through mass spectrometry, and amino-acid analysis.

Other Applications

In a preferred embodiment, the present invention provides a diagnostic composition for imaging amyloid deposits, particularly in a mammalian brain. The diagnostic composition includes a BBB permeant peptide having the amino acid sequence of SEQ. ID. NO.: 1, and coupled to the peptide a chelation core including a medical imaging agent, and a pharmaceutically acceptable excipient or diluent. The medical imaging agent is, for example, a radionuclide, such as technetium-99m or technetium-94m.

The invention also embraces use of the peptides of the present invention, including a method of detecting amyloid plaques in a living mammal involving providing a medical imaging agent coupled to a BBB permeant amyloid-targeting peptide.

Also intended to fall within the present invention is a method of making a BBB permeant amyloid-targeting peptide conjugate labeled with a medical imaging agent. The method involves synthesizing a BBB permeant amyloid-targeting peptide, the amino acid sequence of which comprises SEQ. ID. NO.: 1, coupling a chelation core to the BBB permeant amyloid-targeting peptide, and coupling a medical imaging metal to the chelation core of the BBB permeant amyloid-targeting peptide. The medical imaging metal is, for example, technetium-99m or technetium-94m.

The present invention also provides a method of making a BBB-permeant amyloid-targeting peptide based on a peptide library. The peptide library consists of a plurality of peptides wherein each peptide has a distinct amino acid sequence, each such sequence comprising a partial amino sequence from the full-length Aβ 1-40 amino acid sequence (SEQ. ID. NO.: 2), then testing each peptide for amyloid-targeting specificity and BBB permeability, and comparing the amyloid-targeting specificity and BBB permeability of each peptide to the amyloid-targeting specificity and BBB permeability of the peptide, the amino acid sequence of which comprises SEQ. ID. NO.: 1.

In another aspect, the present invention provides a method for imaging cells in vivo, comprising administering to an animal a cell imaging effective amount of a compound comprising a BBB-permeant peptide conjugate; a chelated radionuclide or a chelated relaxivity metal; and a linker moiety linking the peptide and the chelated radionuclide or the chelated relaxivity metal, and monitoring or evaluating the location of the radionuclide or relaxivity metal within the animal.

In another aspect, the present invention provides a method for imaging cells in vitro, comprising contacting the cells with a cell imaging effective amount of a compound comprising a BBB-permeant peptide; a diagnostic substance; and a linker moiety linking the peptide and the diagnostic substance, and monitoring or evaluating the presence of the diagnostic substance within the cells.

In a further aspect, the present invention provides a method for detecting AD in vivo, comprising administering to an animal a AD detecting effective amount of a compound comprising a BBB-permeant peptide; a diagnostic substance; and a linker moiety linking the peptide and the diagnostic substance, and monitoring the diagnostic substance within the animal.

In another aspect, the present invention provides a method for detecting in vitro, comprising contacting cells or tissue in vitro with an AD detecting effective amount of a compound comprising a BBB-permeant peptide; a diagnostic substance; and a linker moiety linking the peptide and the diagnostic substance, and monitoring the diagnostic substance within the cells or tissue.

In yet another aspect, the present invention provides a method for detecting an enzyme or receptor on a cell, comprising contacting the cell with an enzyme or receptor detecting effective amount of a compound comprising a BBB-permeant peptide; a diagnostic substance; a linker moiety linking the peptide and the diagnostic substance, removing unreacted compound from the locus of the cell so that the signal to noise ratio is sufficient for diagnostic purposes; and monitoring the presence of the diagnostic substance in the cell. Such monitoring can be performed quantitatively, and the cell can be present within a living animal such as in the central nervous system. Furthermore, the enzyme or receptor can be one that is characteristically associated with a disease, condition, or disorder.

The present peptide conjugates can also be used in fluorescence resonance energy transfer (FRET) to study intracellular processes. When used with the FRET methodology, a functional linker is placed between a fluorescent energy donor and acceptor. Examples of suitable pairs of fluorescent energy donor and acceptors, as well as methods for using FRET, are well known in the art and are described (Blomberg et al., 1999; Jamieson et al., 1999; Ubarretxena-Belandia et al., 1999).

In addition to providing compositions and methods for medical imaging, other diagnostic methods, and drug delivery, the present invention also provides methods for evaluating cellular processes in living cells within the CNS in vivo. Examples of such processes include protein-protein binding, protein kinase activities, protein phosphatase activities, or protease activities. Additional examples include the activities of exo- and endo-peptidases, extracellular metalloproteases, lysosomal proteases such as the cathepsins (cathepsin B), as well as transferases, hydrolases, isomerases, ligases, oxidoreductases, esterases, glycosidases, phospholipases, endonucleases, ribonucleases and β-lactamases as they relate to the various disease states associated with loss of function or gain of function for each. These methods are performed by administering agents that are translocated across the BBB and which are detectable in living cells despite the presence of biological tissue intervening between the detection device and the cells in their in situ location. Thus, cells in the living body or in a tissue mass are detectable in situ.

In yet another aspect, the present invention provides a method for diagnosing the presence of a disease, condition, or disorder in an animal, comprising administering to the animal a diagnostically effective amount of a compound comprising a BBB-permeant peptide; a diagnostic substance; a linker moiety linking the peptide and the diagnostic substance wherein the diagnostic substance comprises a sequence reactive with an enzyme, receptor or target indicative or characteristic of the disease, condition, or disorder, and monitoring the diagnostic substance within the animal. By way of example, the disease, condition, or disorder can be a cancer or inflammation such as a central nervous system tumor or metastasis, or a vascular abnormality or infection with a microbe.

In still another aspect, the present invention provides a method of assessing the effectiveness of AD therapy, comprising administering to an animal undergoing AD therapy a diagnostically effective amount of a compound comprising a BBB-Permeant peptide; a diagnostic substance; and a linker moiety linking the peptide and the diagnostic substance, and monitoring the diagnostic substance within the animal. Such monitoring can be performed quantitatively. Furthermore, the method can be repeated at intervals during the AD therapy, and the quantity of the diagnostic substance detected within the animal at each interval can be compared to the quantity of the diagnostic substance detected at previous intervals to determine the effectiveness of the therapy.

In yet another aspect, the present invention provides a method of delivering a pharmacologically active substance to a cell, comprising contacting the cell with an effective amount of a compound comprising a BBB-permeant peptide; a pharmacologically substance; and a linker moiety linking the peptide and the pharmacologically substance, wherein the BBB-permeant peptide confers the ability to penetrate the BBB with the compound. A wide variety of drugs are suitable for use with the present invention, and include, for example, conventional chemotherapeutics, such as vinblastine, doxorubicin, bleomycin, methotrexate, 5-fluorouricil, 6-thioguanine, cytarabine, cyclophosphamide, taxol, taxotere, cis-platin, adriamycin, mitomycin, and vincristine as well as other conventional chemotherapeutics as described in Cancer (Devita et al., 1997). Also suitable for use in the present invention are experimental drugs, such as UCN-01, Glevec, acivicin, 9-aminocamptothecin, azacitidine, bromodeoxyuridine, bryostatin, carboplatin, dideoxyinosine, echinomycin, fazarabine, hepsulfam, homoharringtonine, iododeoxyuridine, leucovorin, merbarone, misonidazole, pentostatin, semustine, suramine, mephthalamidine, teroxirone, triciribine phosphate and trimetrexate as well as others as listed in NCI Investigational Drugs, Pharmaceutical Data 1994, NIH Publications No. 94-2141, revised January 1994.

Other useful drugs include anti-inflammatories such as Celebrex, indomethacin, flurbiprofen, ketoprofen, ibuprofen and phenylbutazone; antibiotics such as beta-lactams, aminoglycosides, macrolides, tetracyclines, pyridonecarboxylic acids and phosphomycin; amino acids such as ascorbic acid and N-acetyltryptophan; antifungal agents; antipsychotics; prostaglandins; vitamins; steroids; and antiviral agents such as AZT, DDI, acyclovir, idoxuridine, amantadine and vidarabine.

Pharmacologically active substances that can be conjugated to the conjugates of the present invention include, but are not limited to, enzymes such as transferases, hydrolyses, isomerases, proteases, ligases, kinases, and oxidoreductases such as esterases, phosphatases, glycosidases, and peptidases; enzyme inhibitors such as leupeptin, chymostatin and pepstatin; and growth factors.

In addition, the present invention can be used to deliver fluorochromes and vital dyes to cells in the central nervous system. Examples of such fluorochromes and vital dyes are well known to those skilled in the art and include, for example, fluorescein, rhodamine, coumadin, Texas red, DAPI, and ethidium bromide.

The delivery of drugs and pharmacologically active compounds across the BBB can be enhanced by direct conjugation to the BBB-permeant peptide and related peptides of the present invention. The coupling of such compounds to a functional linker moiety placed between the BBB-permeant peptide and the active agent, thereby enabling functionally selective trapping of the drug or drug conjugate within the central nervous system, also represents a novel application of the present invention. A drug or prodrug conjugate designed as described herein would enable selective delivery (and retention) of bioactive agents and therapeutic or biologic enhancers useful in therapy including, but not limited to interleukins, tumor necrosis factors, interferons, other cytokines, monoclonal antibodies, immune adjuvants and gene therapy vectors (Devita, 1995), and drugs across the BBB in a manner analogous to the selective trapping of metal chelates as described above. Linker functionality can include any motif that can be acted on by a specific biological activity, such as enzymes, or ribozymes, for example. Examples of such linker functionalities include low molecular weight peptide or protein binding motifs, protein kinase consensus sequences, protein phosphatase consensus sequences, or protease-specific sequences. Protease-reactive or protease-specific sequences are particularly useful in that amplification of the therapeutic effect would occur through enzymatic action on the linker moiety of the drug or prodrug conjugate, thereby releasing the pharmacological agent within the cellular environment of the central nervous system, and increasing the CNS retention and concentration of the agent.

Pharmacologically active substances, anti-inflammatory compounds, anti-AD compounds, cytotoxic substances, diagnostic substances, etc., can be coupled to the appropriate BBB-permeant peptide-linker conjugate through either the amino- or carboxy-terminus of the linker moiety in a manner analogous to that described in U.S. Pat. No. 6,348,185. For example, drug conjugates wherein the carboxy-terminus of the peptide linker is coupled to a bioactive substance can be prepared by the use of an active ester of the desired bioactive substance in the presence of a dehydrating agent. Examples of active esters that can be used in the practice of the present invention include the hemi-succinate esters of N-hydroxysuccinimide, sulfo-N-hydroxy-succinimide, hydroxybenzotriazole, and p-nitrophenol. Dehydration agents include dicyclohexylcarbodiimide (DCC), 1-(3-dimethylaminopropyl)-3-ethylcarbodiimide (ECD), and 1-(3-dimethylaminopropyl)-3-ethylcarbodiimide methiodide (EDCI). The use of ECD to form conjugates is disclosed in U.S. Pat. No. 4,526,714, the disclosure of which is fully incorporated by reference herein. Other examples of coupling reagents include glutathione, 3-(diethoxyphosphoryloxy)-1,2,3-benzotriazin-4(3H)-one (DEPBT), onium salt-based coupling reagents, polyoxyethylene-based heterobifunctional cross-linking reagents, and other reagents that facilitate the coupling of organic drugs and peptides to various ligands (Albericio et al., 1998; Arpicco et al., 1997; Beyer et al., 1998; Deguchi et al., 1998; Dirven et al., 1996; Drouillat et al., 1998; Frisch et al., 1996; Li et al., 1999; Trimble et al., 1997). Chemicals, reagents and techniques useful in drug cross-linking and peptide conjugation are disclosed in general texts well known to those skilled in the art (Dawson et al., 1989; King, 1994; Wong, 1991). Additional chemical coupling agents are described in U.S. Pat. No. 5,747,641, hereby incorporated by reference in its entirety.

In another aspect, the present invention provides a method of treating, inhibiting, or preventing a disease, condition, or disorder responsive to treatment with a pharmacologically substance in an animal, comprising administering to the animal a pharmaceutically effective amount of a compound comprising a BBB-permeant peptide; a pharmacologically substance; and a linker moiety linking the peptide and the pharmacologically substance, wherein the BBB-permeant peptide confers the ability to penetrate the BBB with the compound.

In another aspect, the present invention provides a method for selectively destroying cells expressing a selected enzyme activity or receptor, comprising contacting the cells with a cell-destroying effective amount of a compound comprising a BBB-permeant peptide; a cytotoxic substance; and a linker moiety linking the peptide and the cytotoxic substance, wherein the BBB-permeant peptide confers the ability to penetrate the BBB with the compound.

In yet another aspect, the present invention provides a method for assessing the effect of a drug in altering the expression or activity of an enzyme or receptor in a target cell, comprising contacting the target cell with a diagnostically effective amount of a compound comprising a BBB-permeant peptide; a diagnostic substance; a linker moiety linking the peptide and the diagnostic substance wherein the diagnostic substance comprises a sequence capable of interacting with the enzyme or receptor so as to bind the diagnostic substance to the cell; clearing unreacted compound from the locus of the cell so that the signal to noise ratio is sufficient for diagnostic purposes; and monitoring or evaluating the diagnostic substance in the target cell. Such monitoring can be performed quantitatively, and the target cell can be present within a living animal. Furthermore, the enzyme or receptor can be associated with a disease, condition, or disorder.

In yet another aspect, the present invention provides a method for detecting the expression of a nucleic acid sequence, which can be DNA or RNA, encoding an enzyme, a receptor, or a binding protein introduced into a cell, comprising contacting the cell with a compound comprising a BBB-permeant peptide; a diagnostic substance; a linker moiety linking the peptide and the diagnostic substance which comprises a sequence capable of interacting with the enzyme, receptor, or binding protein so as to selectively retain the diagnostic substance in or on the cell, and monitoring the diagnostic substance in the cell.

The present invention also provides a method of imaging amyloid deposits in a mammal wherein a detectable quantity of a diagnostic composition as previously described is introduced into the mammal, allowing sufficient time for the composition to become associated with amyloid deposits, and then detecting the labeled compound associated with one or more amyloid deposits.

Thus, as explained in more detail in the Examples infra, the novel BBB-permeant peptide with appended chelation core provides a template that is well-suited to further modification and generation of readily available multimodality imaging probes for noninvasive diagnosis of Aβ fibrils in brain. For example, the BBB permeant peptide with appended chelation core provides a necessary platform for designing Aβ-targeted probes capable of accommodating other isotopes. In addition, the BBB permeant peptide with appended chelation core is adaptable to generation of dual-modality imaging probes for use with MR/PET, MR/Optical, PET/Optical, and SPECT/PET imaging.

Therefore, the present invention also embraces modifications of a BBB permeant Aβ-targeted peptide. For example, a Tc-99m-labeled BBB permeant peptide is convertible to a PET agent by using Tc-94m ($t_{1/2}$=53 min) instead of Tc-99m and making use of standard ligand exchange procedures. Further, the BBB permeant Aβ-targeted peptide is amenable to incorporation with hydrophobic fluorophores to further enhance target specificity. Such a strategy also allows incorporation of scaffolds such as 1,4,7,10-tetraazacyclododecane-1,4,7,10-tetraacetic acid (DOTA) and DTPA to accommodate PET isotopes, such as copper-64 (Cu-64 ($t_{1/2}$=12.8 h), for prolonged evaluations) or gallium-68 (Ga-68 ($t_{1/2}$=68 min), for intermediate evaluations) for enhanced spatial resolution and quantification capabilities. BBB permeant Aβ-targeted peptides in accordance with the present invention also accommodate paramagnetic metals s70uch as gadolinium for MRI interrogation of amyloid binding in vivo. In addition, these peptides provide a versatile platform technology for multimodality imaging of Aβ using dual labeled peptides for PET/MR or PET/Optical imaging. Thus, this new approach provides a class of imaging agents with the potential to provide an array of efficient diagnostic tools for detection of Aβ in living patients, as well as for monitoring of progress for patients undergoing standard or experimental anti-amyloid therapies.

BBB permeant Aβ-targeted peptides in accordance with the present invention include Tc-99m-labeled Aβ-targeted peptides which are readily synthesized and characterized through various analytical and spectroscopic techniques. Tc-99m-labeled Aβ-targeted all D-peptide was found to be stable in human serum, thus activity of this peptide is mediated by the intact radiopharmaceutical per se. Tc-99m-labeled Aβ-targeted D-peptide shows binding with Aβ fibrils. In addition, binding to fibrils is concentration-dependent, saturable, and displaceable to background conditions with either unlabeled peptide or cold Re-peptide, indicating target specificity. Tc-99m-labeled peptides demonstrate translocation across RBE4 cells in transwell configuration, thereby indicating the ability to bypass the blood-brain barrier. Quantitative biodistribution studies in normal mice show a transient uptake of the $^{99m}$Tc-peptide in brain at 5 min post tail-vein injection, a value comparable to that of a brain permeant dye 11C-methoxy-X34 (Klunk et al., 2002), followed by complete washout. The Aβ-targeted peptide, conjugated with FM, shows staining of plaques in the cortical region of brain sections in APPsw+/− mice compared with none in WT mice. Like other aggregates, Aβ fibrils are also formed through combination of intermolecular and intra-molecular forces, thus the cold peptide invented herein as well as their modified analogues would have potential to serve as competing donor sites to fibrils thus slowly disintegrating those aggregates, thus these peptides would have a potential utility as therapeutics. As a first step towards their evaluation as therapeutics, unlabeled peptide or Re-peptide is nontoxic to mice following intravenous tail-vein injection at a dose of 14 mg/kg, a value 10,000-fold higher than required imaging doses and is within the therapeutic window for a possible therapeutic drug.

The methods of the bioassays used for evaluating target specificity and toxicity are described, using $^{99m}$Tc-labeled peptides or dual-labeled imaging probes under various conditions. However, any BBB permeant Aβ-targeted peptide according to the present invention can be readily evaluated with such bioassays. Suitable bioassays in general include, for example, a) Aβ binding assays in vitro; b) autoradiography and staining studies with AD brain sections; c) pharmacokinetic analysis and biodistribution studies in mice; and d) noninvasive imaging studies of Aβ formation in vivo in control mice and APPsw$^{+/-}$ transgenic mice.

Formulations/Pharmaceutical Compositions

The compounds of the present invention can be formulated as pharmaceutical compositions. Such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, (Hoover, 1975; Liberman and Lachman, 1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Suppositories for rectal administration of the compounds discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Solid dosage forms for oral administration may include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form will vary depending upon the patient and the particular mode of administration.

Pharmaceutically Acceptable Salts of Peptide Conjugates

Like amino acids, peptides and proteins are ampholytes, i.e., they act as both acids and bases by virtue of the presence of various electron-donor and acceptor moieties within the molecule. The peptide conjugates of the present invention can therefore be used in the free acid/base form, in the form of pharmaceutically acceptable salts, or mixtures thereof, as is known in the art. Such salts can be formed, for example, with organic anions, organic cations, halides, alkaline metals, etc.

The term "pharmaceutically acceptable salts" embraces salts commonly used to form alkali metal salts and addition salts of free acids or free bases. The nature of the salt is not critical, provided that it is pharmaceutically acceptable. Suitable pharmaceutically acceptable base addition salts of the present peptide conjugates include metallic salts and organic salts.

Preferred metallic salts include, but are not limited to, appropriate alkali metal (group Ia) salts, alkaline earth metal (group IIa) salts, and other physiologically acceptable metals. Such salts can be prepared, for example, from aluminum, calcium, lithium, magnesium, potassium, sodium, and zinc.

Organic salts can be prepared from tertiary amines and quaternary ammonium salts, including in part, tromethamine, diethylamine, N,N'-dibenzyl-ethylenediamine, chloroprocaine, choline, diethanolamine, ethylenediamine, meglumine (N-methyl-glucamine), and procaine.

Such salts can also be derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate, and undecanoate.

The basic nitrogen-containing groups can be quaternized with agents such as lower alkyl halides, such as methyl, ethyl, propyl, and butyl chloride, bromides, and iodides; dialkyl sulfates such as dimethyl, diethyl, dibuytl, and diamyl sulfates; long chain halides such as decyl, lauryl, myristyl, and stearyl chlorides, bromides, and iodides; aralkyl halides such as benzyl and phenethyl bromides, and others.

All of these salts can be prepared by conventional means from the corresponding peptide conjugate disclosed herein by reacting the appropriate acid or base therewith. Water- or oil-soluble or dispersible products are thereby obtained as desired.

Doses/Quantities of Peptide Conjugates

The quantity of BBB-permeant peptide conjugate comprising a radionuclide for use in radiolabeling and imaging, or relaxivity metal, should be an effective amount for the intended purpose. Such amounts can be determined empirically, and are also well known in the art. For example, amounts of radionuclide administered via the present conjugates can be in the range of from about 1 µCi to about 100 mCi, preferably from about 1 mCi to about 100 mCi, and more preferably from about 1 to about 50 mCi. This amount can be adjusted for body weight and the particular disease state, and can be about 1 mCi/kg body weight.

For therapeutic purposes, the amount of radionuclide administered via the present conjugates can be in the range of from about 1 mCi to about 300 mCi, preferably from about 25 mCi to about 250 mCi, and more preferably from about 50 mCi to about 200 mCi. Of course, this amount can be tailored to meet the specific requirements of the disease state being treated, and can also vary depending upon the weight and condition of the patient as is well known in the art. Note, for example, (Maisey et al., 1998).

The amount of conjugate comprising a drug or other pharmacologically active agent for administration to a patient to treat or prevent a disease condition will vary with the type of drug, and will comprise a therapeutically effective amount thereof. Drug dosages for treating various conditions are well known in the art. Note in this regard, for example, (Goodman et al., 1996).

Routes of Administration

The conjugates of the present invention can be administered by a variety of methods, including, for example, orally, internally, mucosally, percutaneously, intravascularly or parenterally. Parenteral administration is preferred, especially by intravenous, intramuscular, subcutaneous, intracutaneous, intraarticular, intrathecal, and intraperitoneal infusion or injection, including continuous infusions or intermittent infusions with pumps available to those skilled in the art. Alternatively, the conjugates can be administered by means of micro-encapsulated preparations, for example those based on liposomes as described in European Patent Application 0 213 523.

Treatment Regimens

The regimen for treating a patient with the compounds and/or compositions of the present invention is selected in accordance with a variety of factors, including the age, weight, sex, diet, and medical condition of the patient, the severity of the condition, the route of administration, pharmacological considerations such as the activity, efficacy, pharmacokinetic, and toxicology profiles of the particular pharmacologically active compounds employed.

Administration of the drug peptide conjugates disclosed herein should generally be continued over a period of several days, weeks, months, or years. Patients undergoing treatment with the drug peptide conjugates disclosed herein can be routinely monitored according to common clinical practice to determine the effectiveness of the therapy for the particular patient and disease or condition in question.

Continuous analysis of the data obtained by these methods permits modification of the treatment regimen during therapy so that optimal amounts of the pharmacologically active substance in the peptide conjugate are administered, and so that the duration of treatment can be determined as well. Thus, the treatment regimen/dosing schedule can be rationally modified over the course of therapy so that the lowest amounts of drug compound is administered, and so that administration of such compounds is continued only so long as is necessary to successfully treat the disease or condition.

Monitoring Devices/Procedures

Detection methods useful in practicing the present invention include, but are not limited to magnetic resonance, fluorescence imaging, near infrared optical imaging, optical tomography, bioluminescence, superconducting quantum interference device (SQUID), planar scintigraphy or single photon emission computed tomography (SPECT), and in particular, positron emission tomography (PET). Alternative methods of detection include gamma counting, scintillation counting, scanning radiograms, densitometry and fluorography. These detection methods can be employed during or after an effective time interval for diagnosis or imaging subsequent to administering a peptide conjugate of the present invention. Such effective time intervals are well known in the art, or can be readily determined employing methods such as those disclosed herein.

Kit Formulations

The present invention further provides a kit comprising a compound comprising a BBB-permeant Aβ-targeted peptide; a metal chelation ligand; and a linker moiety linking the peptide and the metal chelation ligand, and a reducing agent capable of reducing a metal that can be coordinately incorporated into the metal chelation ligand. Typically, these kits would be prepared with a predetermined amount of Aβ-targeted peptide and a reducing agent that is capable of reducing a predetermined quantity of a selected radionuclide to a desired oxidation state appropriate for complexation. Such kits can contain a predetermined quantity of glucoheptonate, for example. Furthermore, both Aβ-targeted peptide and a reducing agent can be lyophilized to enable a long shelf life, which can be further enhanced by storing at −20 degrees C. The Aβ-targeted peptide and a reducing agent can be sealed in a sterilized container possessing instructions for handing and reactions prior to injections. Thus, in one embodiment, this invention provides a kit for use in preparing an Aβ-targeted diagnostic agent. Thus, prior to use, Tc-99m-pertechnetate can be eluted from a Tc/Mo generator commonly present in nuclear medicine facilities and hospital radiopharmacies with isotonic sterile saline, and the Aβ-targeted peptide treated with Tc-99m-pertechnetate in the presence of a reducing agent such as stannous chloride or sodium dithionite to reduce a selected quantity of Tc-99m pertechnetate, and thereby, obtain the desired Tc-99m-peptide conjugates. In addition, the kit can also include a requisite amount of a selected peptide to react with an appropriate amount of reduced Tc-99m supplied in the kit in form of $^{99m}$Tc-glucoheptonate (Dupont Pharma), and a reducing agent such as sodium dithionite or stannous chloride sufficient enough to reduce the desired quantity of technetium to produce Aβ-targeted $^{99m/94m}$Tc-peptide.

EXAMPLES

Without further elaboration, it is believed that one skilled in the art can, using the preceding description, utilize the present invention to its fullest extent. The following specific examples are offered by way of illustration and not by way of limiting the remaining disclosure.

Example 1

Synthesis of Permeation Peptides

BBB permeation peptides were synthesized based on short peptides incorporating the sequence KLVFF that were known to bind to Aβ (Tjernberg et al., 1997). A D-permeation probe was designed in part using the sequence KLVFF, and by using three functional constituents: a) an amyloid targeted-peptide sequence; b) a linker moiety; and c) a peptide-based chelation core for incorporation of technetium-99m for medical imaging (FIG. 1a). A peptide having the final overall amino acid sequence KKLVFFAεKGC (SEQ. ID. NO.: 1) was prepared by coupling the amino acids using solid-phase peptide synthesis (SSPS) using L- or D-N-α-FMOC-protected amino acid residues and standard coupling techniques as described in more detail supra.

The peptide was purified on a semi-preparative C-18 column (Xterra) using Water's HPLC system equipped with dual A detector (2487) set to 214 and 280 nm. The fraction eluting at $R_t$=13.6 min was collected, lyophilized, and analyzed through amino acid analysis and electron spray mass spectrometry (ESMS). The amino acid analysis was found to be consistent with the proposed formulation. In addition, ESMS of the HPLC fractions confirmed the identity of the peptide (ESMS: Calcd for $C_{57}H_{92}N_{14}O_{11}S_1$: 1181.5; Found 1182.4). Because it is well established that rhenium metal acts as a surrogate for technetium, we synthesized the rhenium peptide using standard ligand exchange procedures as established in other and our laboratories (Lister-James, 1997a; Lister-James, 1997b; Polyakov, 2000).

Example 2

HPLC Characterization of Peptides

Figure 2:
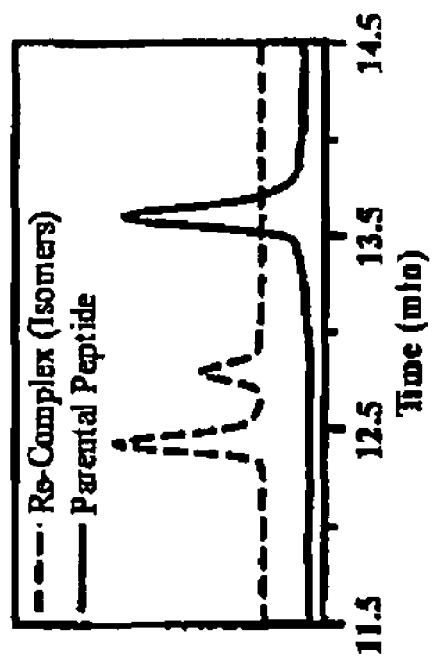
FIG. 2 is a graph of HPLC (high performance liquid chromatography) data of a parental peptide and a rhenium-peptide complex (two peaks represent two isomers) under the same gradient conditions.

For characterization, RP-HPLC was performed, the requisite fractions isolated and their identities confirmed through electron spray mass spectrometry (FIG. 2). Both peaks ($R_t$=12.4; 12.8 min) with Re-peptide demonstrated identical mass [ESMS: calcd for $C_{57}H_{89}N_{14}O_{12}ReS$: 1380.6; Found: 1381 ($R_t$=12.4 min; peak A); 1381 ($R_t$=12.8 min; peak B)]. Thus, the peaks represented the existence of two isomers of the $N_3S$ chelation moiety in relation to the metal-oxygen bond, due to participation of the chiral α-C atom of lysine in the chelating ring. The formation of the two anticipated diastereoisomers (the apical oxygen being syn and anti relative to the side chain of lysine residue) were consistent with metals in both conjugates, $^{99m}$Tc-peptide or Re-peptides, using an identical chelation core.

Example 3

In Vivo Characterization

To confirm stability under in vivo conditions, the peptide was radiolabeled with technetium-99m through a ligand exchange procedure using $^{99m}$Tc-glucoheptonate and the desired fraction separated through Radio-RP-HPLC. The $^{99m}$Tc-labeled peptide was incubated in human serum at 37° C. for 3 h. Thereafter, Radio-TLC analysis using a radiometric detection system (Bioscans 2000) was performed to evaluate the presence of metabolites in the mixture. The $^{99m}$Tc-peptide demonstrated persistence of the parental peptide only, thereby indicating stable incorporation of the radiometal within the chelation core (FIG. 3).

Example 4

Binding Assays

1. Binding Assays

Figure 4:
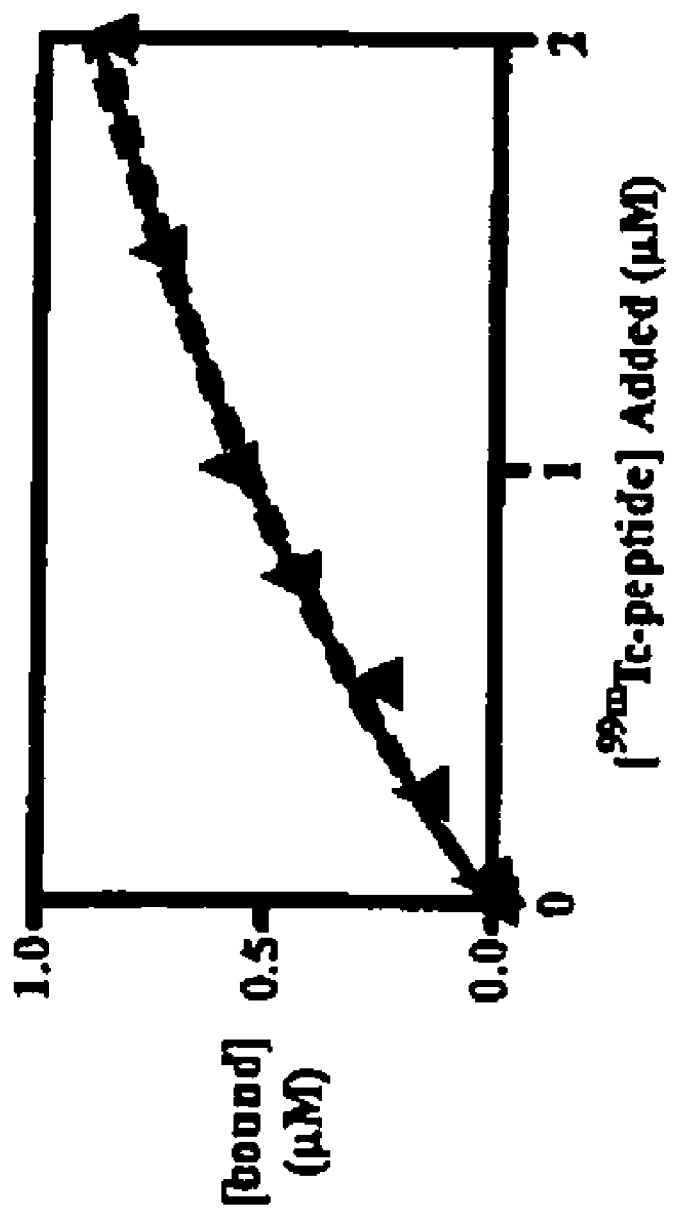
FIG. 4 is a graph describing binding of the lead $^{99m}$Tc-peptide to preformed Aβ 1-40 aggregates.

Binding assays of $^{99m}$Tc-peptide with Aβ fibrils were performed in PBS. The radiolabeled peptide was incubated with fibrils at RT for 90 min. The aggregate-bound $^{99m}$Tc-peptide was separated on Centricon filter units (100 KDa cut off) and washed three times with PBS buffer. The concentration of aggregate-bound $^{99m}$Tc-peptide was calculated on the basis of activity retained on the filters. Each data point represents a mean of triplicate measurements. The data indicated saturable binding with a $K_d$=352±82 nM (FIG. 4).

2. Competitive Binding

Figure 5:
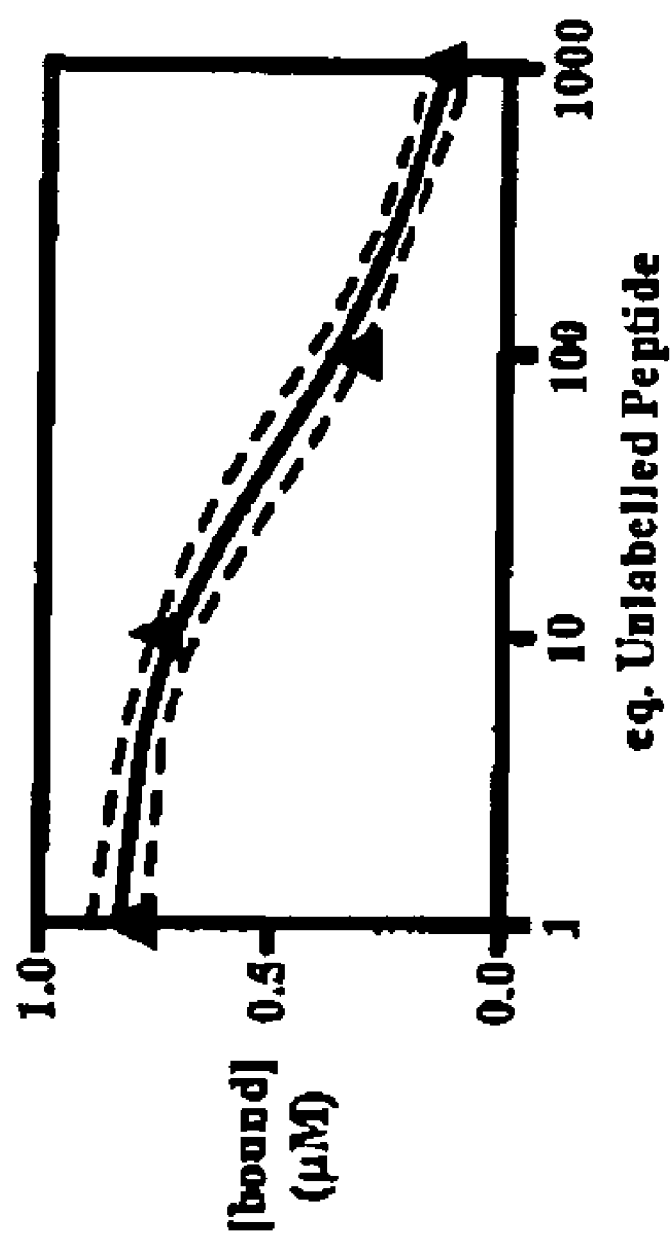
FIG. 5 is a graph of results of a competitive binding assay evaluating binding of a $^{99m}$Tc-peptide to Aβ 1-40 fibrils in the presence of increasing amounts of unlabeled peptide.

Binding of the lead $^{99m}$Tc-peptide to preformed Aβ 1-40 aggregates in presence of increasing equivalents of unlabeled competing peptide. The aggregate-bound $^{99m}$Tc-peptide was isolated from free labeled peptide by centrifugation using Centricon (100 kDa cutoff) filters. The concentration of aggregate bound $^{99m}$Tc-peptide was calculated on the basis of activity retained on the filters (FIG. 5).

The competitive binding assays demonstrated that the radiolabeled peptide was displaceable to background conditions with either 1,000-fold molar excess of unlabeled peptide or cold Re-peptide, further supporting receptor-like binding behavior of the peptide to Aβ fibrils. Each data point represents a mean of triplicate measurements.

Example 5

Peptide Permeation

Imaging in living patients mandates that probes be able to permeate the blood-brain barrier (BBB). Brain capillary endothelial cells possess tight junctions and vectorial transporters, thereby creating a barrier for drugs, ions, proteins, and cytotoxins. Immortalized rat brain endothelial cells (RBE4) have been established as a valid in vitro model of the BBB (Mroczkowsa et al., 2000) and were used for transport experiments.

Figure 7:
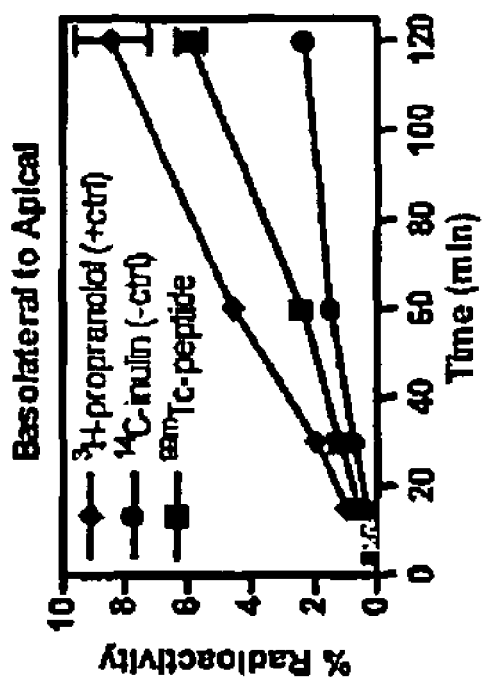
FIG. 7 is a graph describing basolateral to apical transendothelial transport of the $^{99m}$Tc-peptide, including each point representing buffer radioactivity in the trans-chamber as a percent of radioactivity added to the cis chamber (means of triplicate determinations).
Figure 6:
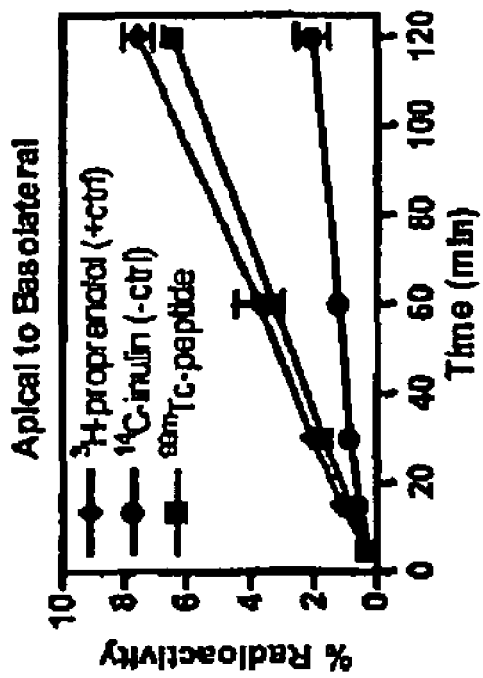
FIG. 6 is a graph describing apical to basolateral transendothelial transport of the $^{99m}$Tc-peptide, including each point representing buffer radioactivity in the trans-chamber as a percent of radioactivity added to the cis chamber (means of triplicate determinations).
Figure 8B:
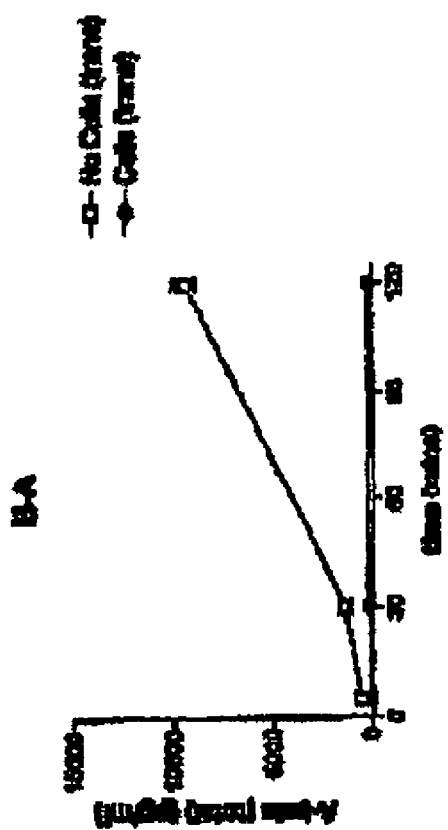
FIG. 8b is a graph describing basolateral to apical transendothelial transport of $^3$H-Aβ1-40 peptide across RBE4 cells, including each point representing the quantity of peptide (pg/ml) in the trans-chamber.
Figure 8A:
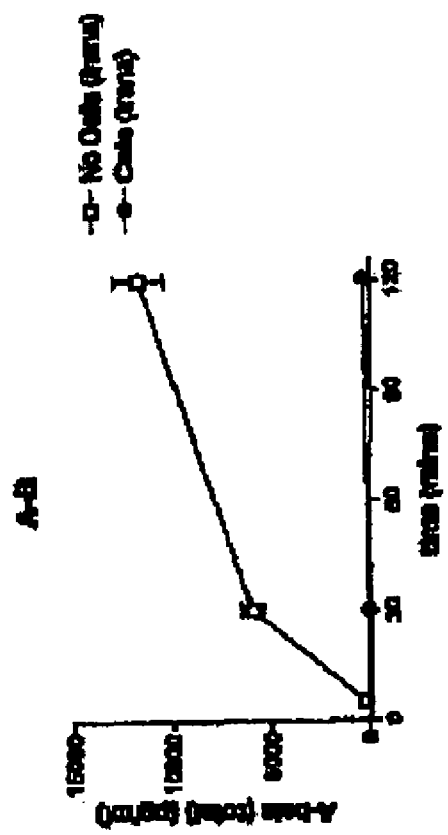
FIG. 8a is a graph describing apical to basolateral transendothelial transport of $^3$H-Aβ1-40 peptide across RBE4 cells, including each point representing the quantity of peptide (pg/ml) in the trans-chamber.

Under triple-label conditions, $^{14}$C-inulin, $^3$H-propranolol, and $^{99m}$Tc-peptide were added to RBE4 cell monolayers (FIGS. 6 & 7). The $^{14}$C-inulin, a macromolecular marker (negative control) was used for monitoring paracellular leak pathways present in the cell monolayers [Violini, 2002 #4113], and showed low transwell transport, thereby confirming the presence of tight junctions and barrier formation with the RBE4 cells. In contrast, $^3$H-propranolol (positive control), a diffusible hydrophobic compound, showed high transcellular permeation in RBE4 cells. Finally, $^{99m}$Tc-peptide showed permeation in this transwell configuration regardless of vectorial preferences. By comparison, full length $^3$H-Aβ1-40 peptide did not show any transwell transport in RBE4 cells, at least under short periods of time up to 120 minutes (FIGS. 8A & 8B).

These results were consistent with published observations that imaging agents based upon full length Aβ1-40 would need the administration of mannitol to permeate the BBB [Wadghiri, 2003 #4212]. However, robust transwell permeation was observed with the lead $^{99m}$Tc-decapeptide. Thus, in RBE4 cells cultured to confluence on collagen filter inserts in transwell configuration, investigations revealed transwell permeation of our $^{99m}$Tc-peptide.

Example 6

Target Specificity

Biodistribution studies in normal mice have revealed a transient uptake of the $^{99m}$Tc-peptide in brain [5 min post tail-vein injection value of 11.79±4.55% IDI (injected dose index)], comparable to that of a brain permeant dye $^{11}$C-methoxy-X34 (Klunk et al., 2002). This was followed by complete washout over the subsequent 60 minutes. These in vivo data support the in vitro transwell data indicating permeation of the $^{99m}$Tc-peptide across the BBB.

Figure 9B:
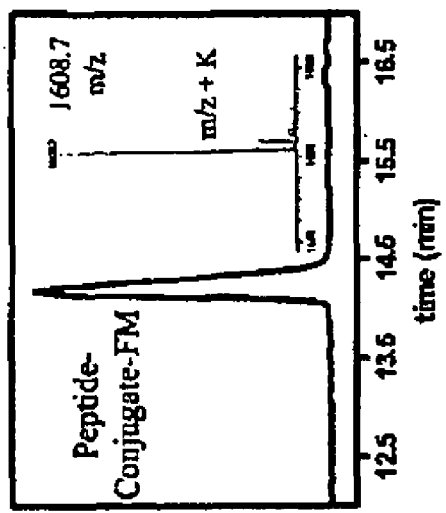
FIG. 9b shows HPLC and mass spectrum for the BBB permeant peptide labeled with FM.
Figure 9A:
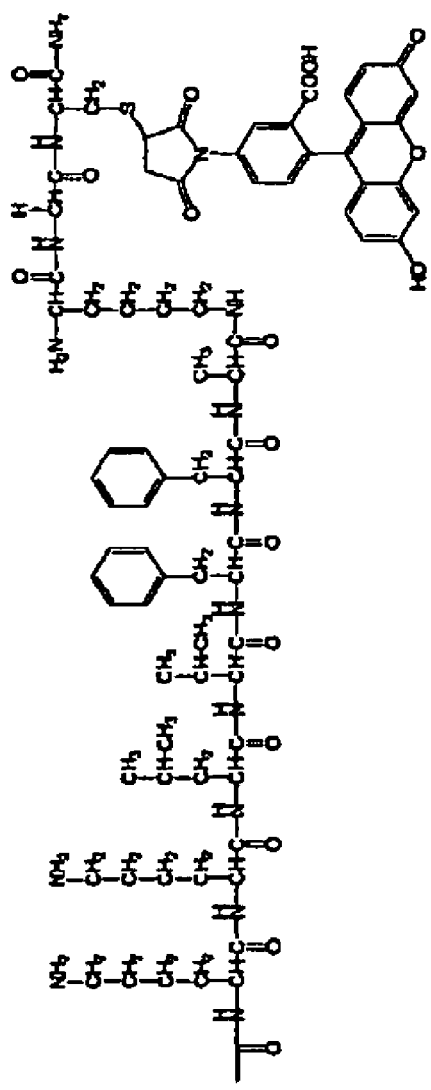
FIG. 9a shows the chemical structure of a BBB permeant peptide labeled with FM.
Figure 10:
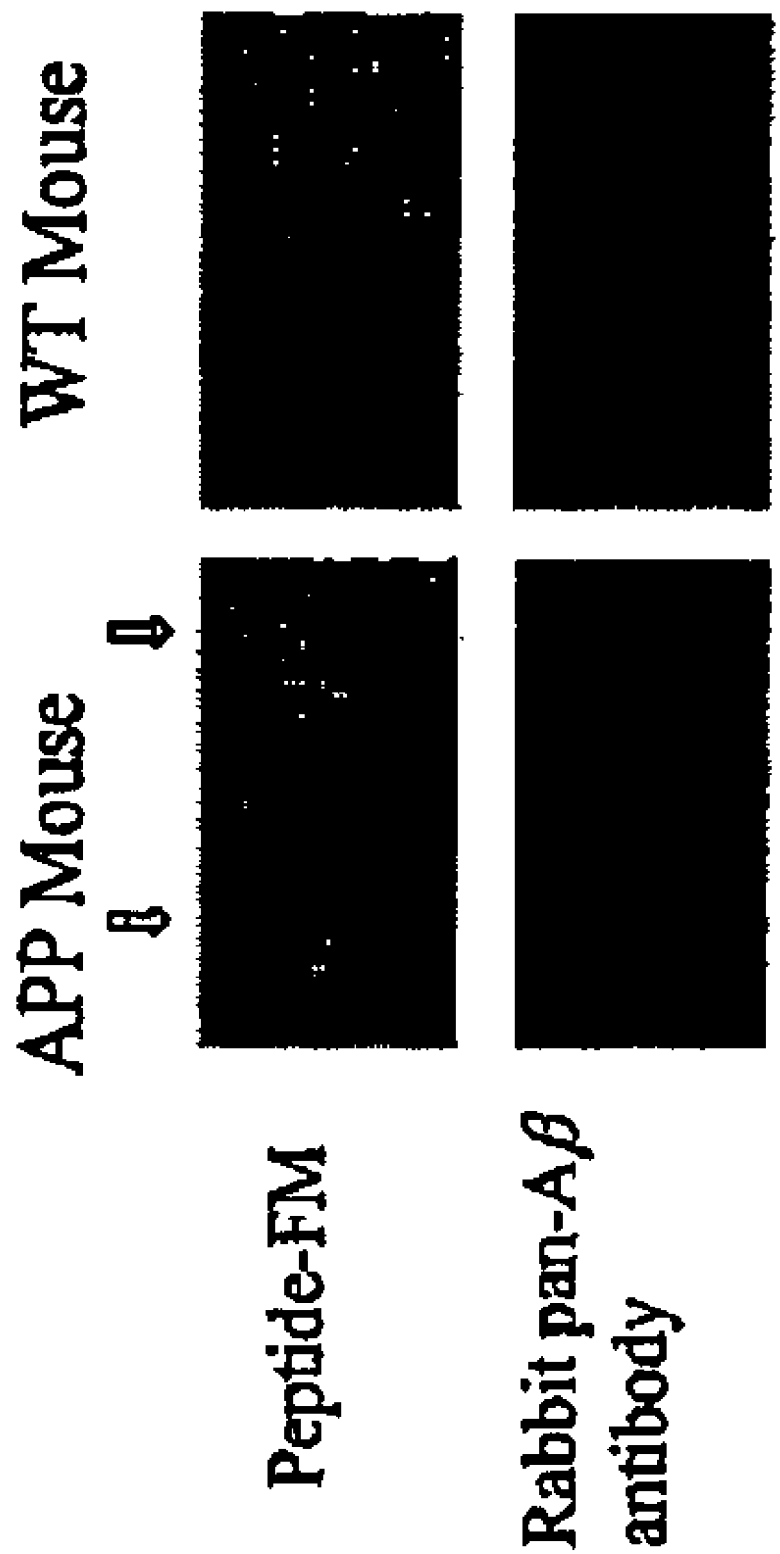
FIG. 10 shows staining of brain tissue sections from APPsw+/− mice and WT mice using an Aβ targeted FM-labeled BBB permeant peptide, and anti-Aβ antibody, with the arrows indicating staining of amyloid plaques in brain sections.

Staining experiments with cross sections of brain tissue were also performed. Peptide was labeled on the C-terminal thiol with fluorescein-5-maleimide (FM; 3-equiv) in DMF (FIG. 9A) at room temperature in the dark, purified on a C-18 column, and fractions eluting at 14.2 min (FIG. 9B) were combined, lyophilized and characterized through electron spray mass spectrometry (ESMS: calcd for $C_{81}H_{105}N_{15}O_{18}S$: 1607.7; Found: 1608.7). For tissue staining, well-established procedures were used both for immunohistochemical staining of Aβ and for FM-peptide staining (DeMattos et al., 2002; Holtzman et al., 2000). Staining was performed on brain sections (40 μm) of an APPsw+/− mouse (17 months old) and a control WT mouse (Bl/6; 13.5 months old). As a control, rabbit-anti-pan Aβ antibody (Biosource International; 1:200 dilution of 100 μl stock in 1% milk-PBS 60 min) was visualized with anti-rabbit antibody conjugated with Alexa 568 (Molecular probes; 1:400 in 1% milk-PBS 90 min). Brain sections of APPsw+/− mice showed immunostaining of Aβ compared with none in WT mouse (FIG. 10). Similarly, using the Aβ-binding peptide coupled with FM (2 μM solution), staining of plaques in the cortical region of brain sections in APPsw+/− mice was observed. By comparison, no staining in WT mice was seen, indicating the targeting specificity of the peptide.

Example 7

Toxicity

Although absolute concentration of radiotracers in vivo is normally too low to cause any host toxicity, nevertheless host safety is a key determinant for any successful diagnostic agent. Therefore, using a Re-labeled peptide as a surrogate for a Tc-labeled peptide, acute toxicity in mice (Balb/C; male; 6-8wks old) was determined. Results on intravenous bolus injection indicated that both Re-peptide or unlabelled peptide (14 mg/kg; a dose 10,000 times required for binding Aβ in vitro) were nontoxic in mice up to several days post-injection.

Example 8

Chemical Synthesis and SAR of Modified BBB Permeant Aβ-Targeted Peptides

Figure 11:
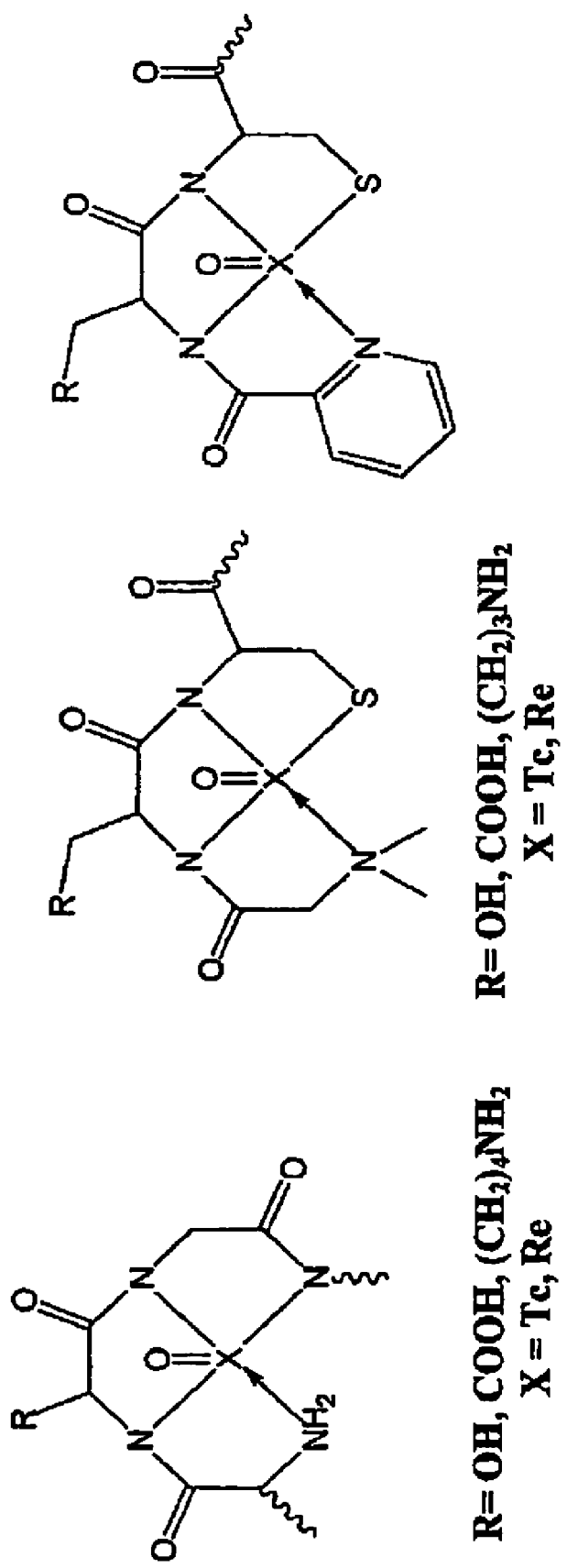
FIG. 11 shows the chemical structures of three alternative chelation cores that accommodate technetium.

BBB permeant Aβ-targeted peptides were obtained by solid-phase peptide synthesis using L- or D-N-α-FMOC-protected amino acid residues using standard coupling techniques. Structure-activity relationships (SAR) are typically used to further characterize candidate bioactive molecules, and comparative SAR of related molecules is especially useful. While keeping the permeation motif unchanged, the other two functional components can be varied and the resulting molecules characterized according to SAR. SAR studies include variations in two of the functional components of the imaging agent: a) the chelation core and b) the amyloid targeted peptide. Further modification can also include synthesis of D-inverso, retroinverso, and scrambled sequences (of the amyloid targeted region) to evaluate its impact on targeting properties. In addition, the permeation motifs and chelation core can be swapped from N-terminus to C-terminus to evaluate any positional or steric preferences on Aβ-targeting properties. Because the coordination chemistry of technetium and rhenium are essentially similar (Liu and Edwards, 1999), if not commonly identical, labeled peptide conjugates are obtained through a ligand exchange method using technetium-99m- or cold rhenium-glucoheptonate (Lister-James et al., 1997b; Polyakov et al., 2000). All peptides are purified by RP-HPLC, characterized through mass spectrometry, and amino-acid analysis.

Example 9

Modification of Tri-peptide Chelation Core

Technetium is especially well-suited for applications according to the present invention because it allows: a) quantitative characterization studies in vitro within a relatively short half-life (6 hours), b) an ideal photon energy for medical imaging, and c) easy access (readily available from a $^{99}$Mo/$^{99m}$Tc-generator that is found in many hospitals and institutions). Further, the chelation chemistries of rhenium and technetium are similar (Liu and Edwards, 1999), thus allowing synthesis of cold-Re-peptides as analogues of $^{99m}$Tc-peptides for chemical characterization studies. Thus, modifications of BBB permeant targeted peptides (i.e. "tri-peptide chelation cores") include those that allow incorporation of both cold rhenium or radiolabeled technetium in their scaffold through simple transmetallation reactions.

During structural modification, the pharmacokinetics of radiopharmaceuticals can be influenced by selection of a chelation moiety. Thus, chemical modification of this region can influence factors such as blood retention time and excretion routes. The permeation Aβ binding motif contains amino acids that can be protonated under physiological conditions, but the chelation moiety contains a neutral technetium conjugate. Ideally, modified BBB permeant targeted peptides are those that result in generation of neutral technetium conjugates. The examples of chelation cores in FIG. 11 offer interesting alternative tri-peptide scaffolds according to the present invention. The Gly-Ala-Gly offers a donor core that lacks sulfur and will offer capabilities to store the peptide for extended period (greater shelf-life) of time at 4° C. due to lack of formation of disulfides. In addition, an overall neutral technetium conjugate will be obtained. Similarly, existence of hydrophobic dimethyl substituents in dimethyl-Gly-Ser-Cys are matched with a hydrophilic alcohol, yield an additional site for H-bonding and provide an $N_3S$ donor core; however, sulfur needs to be protected for extended storage of peptide solution to avoid disulfide bridging (Wong et al., 1997). Finally, Tc-O(Pic-Ser-Gly) conjugates are stable in free cysteine for over 24 h, thereby providing a scaffold less prone to metabolism in vivo (Rajagopalan et al., 1997). All three scaffolds as shown in FIG. 11 are amenable to solid-phase synthesis. Thus, technetium conjugates with these scaffolds will provide alternative BBB permeant Aβ-targeted peptides according to the present invention.

Example 10

Generation of Small Peptide Libraries for Enhanced Targeting

An exemplary Tc-99m-labeled membrane permeant Aβ-targeted peptide translocates across RBE4 cell monolayers in transwell experiments, and binds to Aβ1-40 fibrils. Full length Aβ1-40 conjugated to a cyclic (DOTA) or non cyclic (DTPA) chelating core is known to have the potential to act as a non-invasive agent, although mannitol is needed to induce permeation through the BBB (Wadghiri et al., 2003). Therefore, other sites of Aβ-targeting within the Aβ sequence can be evaluated by exploring a series of fragments of amino acids with a variation of one amino acid at a time. Fragment lengths could vary from four to perhaps nine amino acids. A small peptide library approach is used to select a fragment of amino acid residues (from Aβ 1-40 peptide) that will provide enhanced targeting properties.

Figure 12:
FIG. 12 is a schematic diagram of a scheme for identifying amino acid sequences coding for BBB permeant peptides with enhanced Aβ target specificity.

All peptides are synthesized from the C-terminus using standard Fmoc chemistry. During this approach with a five amino acid fragment, while one amino acid is varied at a time, the other four amino acid residues represent the overlapping amino acid residues, thus generating a small peptide library in the process (FIG. 12). While retaining the chelating core on the C-terminus, these sequential stepped fragments of pentapeptides are incorporated into the Aβ-targeting region of a lead sequence.

All of these peptides are subject to radiolabel and subsequently can be readily screened as $^{99m}$Tc-peptides. Promising candidate peptides can then be further characterized as Re-peptides. The strategy identifies the specific amino acids that promote or inhibit binding with Aβ1-40. In addition, scrambled sequences are used to evaluate any sequence specificity in Aβ-targeting properties of lead peptides. Both D- and L- as well as retroinverso D- amino acid sequences will be used. All purified peptides will be radiolabeled with Tc-99m using a ligand exchange method and assessed for their ability to bind Aβ1-40 in vitro according to procedures described in Example 4 (see FIGS. 4 and 5), supra.

Example 11

Synthesis of Technetium-94m-Peptides and Copper-64 PET Imaging Probes

The peptides are also amenable to generation of sensitive PET Aβ-targeted agents. Compared with SPECT agents, PET probes offer enhanced resolution and quantification capabilities. The radionuclide Tc-94m with its positron branching ratio of 72%, positron end-point energy of 2.47 MeV, and relatively short half-life of 52 min, is suitable for quantitative measurements using PET.

Tc-94m is produced by proton bombardment of isotopically enriched [Mo-94]$MoO_3$. The Tc-99m, a SPECT isotope, is swapped for Tc-94m, a PET radionuclide, to generate an Aβ-targeted PET agent with no variation in the scaffold.

Figure 13:
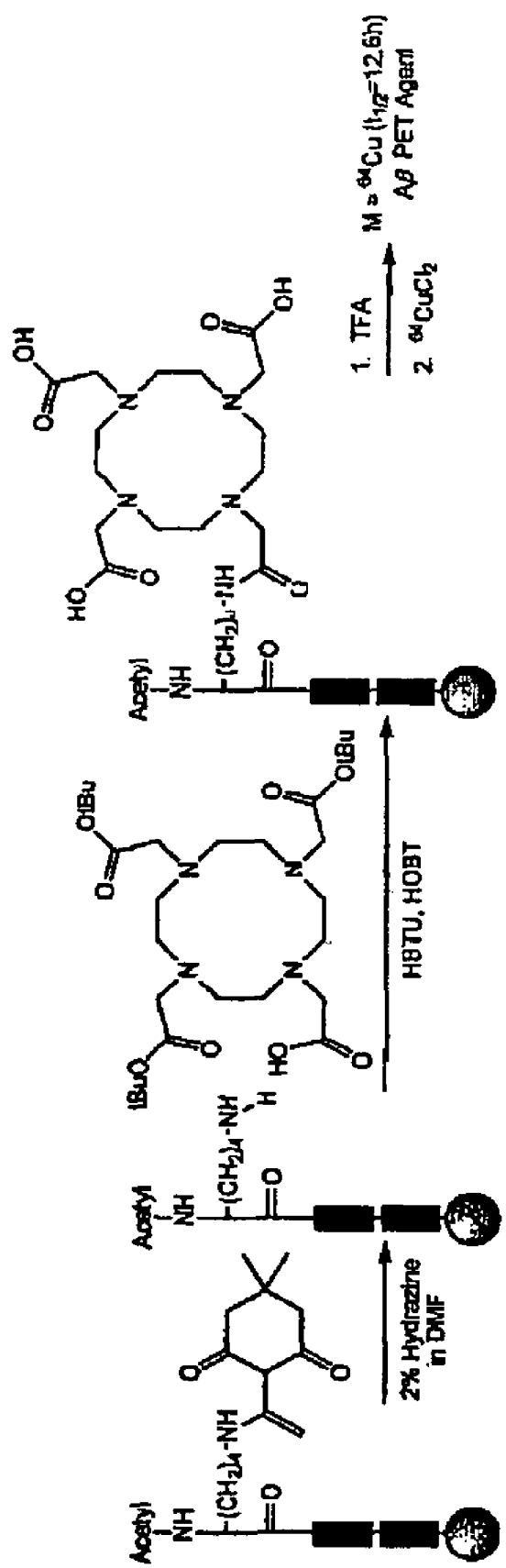
FIG. 13 is a diagram of a scheme for synthesizing an Aβ-targeted BBB permeant copper-64-PET imaging peptide.

Alternatively, chelating macrocyclic compounds, such as DOTA (1,4,7,10-tetraazacyclododecane-1,4,7,10-tetraacetic acid) or acyclic chelator, such as DTPA (diethylene triamine pentaacetic acid) can be incorporated through an orthogonal approach (FIG. 13). These peptides are suitable for providing scaffolds for generation of a copper-based PET agent. Copper-coordinated macrocycles such as DOTA have been shown to be stable.

DOTA is incorporated into the peptide using solid-phase chemistry. Using conventional solid-phase synthetic chemistry, standard side chain protecting groups are retained on all amino acid residues, except for the terminal lysine residue which will contain a (4,4-dimethyl-2,6-dioxocyclohex-1-ylidene)ethyl (Dde) functionality protecting the ε-amino group. This enables an orthogonal synthesis scheme by selective deprotection of Dde with 2% hydrazine while the peptide remains attached to the resin with all remaining protecting groups. The resulting primary amine is coupled with 1,4,7,10-tetraazacyclododecane-1,4,7-tris(acetic acid-t-butyl ester)-10-acetic acid (DOTA-tris(t-butyl ester) using N-hydroxybenzotriazol (HOBt) and O-(benzotriazol-1-yl)-N,N,N',N'-tetramethyluronium hexafluorophosphate (HBTU). Finally, the peptide is cleaved from resin using standard literature procedures and purified on RP-HPLC (Prantner et al., 2003). Purified peptide will be labeled with copper-64 ($t_{1/2}$=12.8 h) by adding peptide to $^{64}CuCl_2$ treated with 0.2 M ammonium acetate, pH 5.0.

Example 12

Synthesis of Aβ-targeted Fluorescent Probes

While radiotracers provide quantification capabilities, microscopic confirmation that these analogues bind plaques in vivo with the desired specificity in the human brain are more appropriately addressed using fluorescent Aβ-targeted peptides. Towards this objective, several Congo Red-based hydrophobic organic molecules have been shown to bind Aβ. Recently, X-34 and methoxy-X-04 derivatized Congo Red based molecules have shown promising Aβ targeting properties (Klunk et al., 2002). Thus, BBB permeant Aβ-targeted peptides in accordance with the present invention also include peptides incorporating such hydrophobic moieties into the scaffold. The derivatized X-34 incorporated peptides offer the following advantages: a) straightforward synthesis using solid-surface chemistry; b) X-34 appended molecules may offer enhanced targeting; and c) incorporation of Tc-99m will make it a more accessible diagnostic probe for clinical applications.

Figure 14:
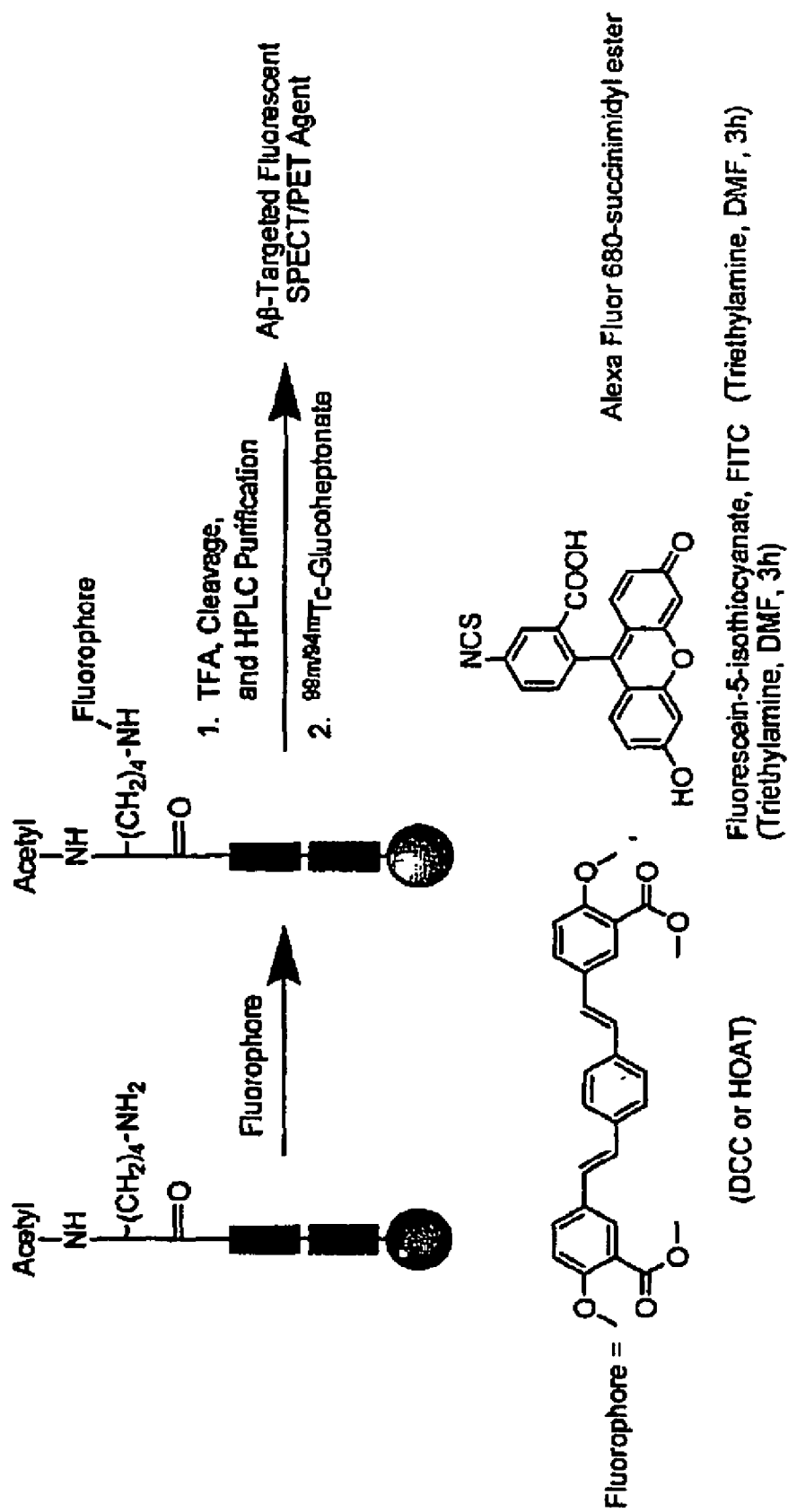
FIG. 14 is a diagram of a scheme for synthesizing an Aβ-targeted fluorescent BBB permeant peptide.

Accordingly, fluorophores can be incorporated into an exemplary BBB permeant Aβ-targeted peptide through solid surface chemistry. The synthetic scheme is provided in FIG. 14. During synthesis, the protecting Dde-group is cleaved with 2% hydrazine and cleavage monitored spectroscopically using UV-Vis spectrophotometry. The deprotected amine is coupled with an ester derivative of X-34 using coupling reagents such as DCC or HOAT in dark. After coupling is complete, resin-containing peptide is washed three times with DMF: water (1:1), DMF, MeOH, ether, and dried. The peptide on resin is cleaved by stirring the resin in TFA cocktail at room temperature in the dark. After 3 h, the solution is filtered into ether (pre-cooled to −78° C.) to obtain precipitates. The precipitates are washed with ether, purified using a C-18 column on HPLC, and characterized through ESMS.

A similar approach is suitable for incorporating fluorescein-5-isothiocyanate (FITC) into the primary amine of lysine. Briefly, the FITC (3-4 equiv) is dissolved in DMF and transferred to Dde deprotected resin. The suspension is stirred for 3 h. The resin is separated in the dark, and washed with DMF to remove any free FITC. Peptide appended with FITC is cleaved and purified using the method described above in Example 11.

The same strategy is suitable for incorporating motifs in the near-IR region (600-800 nm). Light in the near-infrared region is not absorbed by tissues, so that a BBB permeant Aβ-targeted peptide appended with, for example, Alexa Fluor 680 (Molecular Probes) can provide decreased interference of signal from tissues, and enhance the results obtained through staining experiments. This approach is also suitable for use of the scaffold for optical imaging in vivo. For example, the free primary amine (FIG. 14) can be conjugated with a commercially available succinimidyl-ester of Alexa Fluor 680 (Molecular Probes) using DCC in the presence of triethylamine on a solid phase. After coupling, peptide is cleaved in TFA cocktail, purified using a C-18 column on HPLC, characterized through electron-spray mass spectrometry (ESMS) and chelated with Tc-99m through a transmetallation reaction using $^{99m}$Tc-glucoheptonate to generate a dual labeled peptide. BBB permeant Aβ-targeted peptide appended to hydrophobic molecules such as derivatized X-34, FITC and Alexa Fluor 680 are suitable for use as probes for ex-vivo staining of brain tissues from WT mice and APPsw+/− transgenic mice.

Example 13

Metabolic stability of $^{99m}$Tc-peptides or Dual-labeled Peptides

Results show that an exemplary BBB permeant Aβ-targeted peptide, $^{99m}$Tc-peptide, is stable in vitro and in vivo. Alternative BBB permeant Aβ-targeted peptides in accordance with the present invention are evaluated for metabolic stability both in vitro and in vivo using procedures established by the inventors. Briefly, in a typical in vitro stability experiment, exemplary $^{99m}$Tc-peptides or dual-labeled analogues are incubated in serum or cells at time points corresponding to uptake in vivo (2 min to 2 hr), radiotracer is extracted from lysed cells or serum, and is analyzed both by radio-TLC and RP-HPLC equipped with a radio-detector. Similarly, for in vivo experiments, candidate BBB permeant Aβ-targeted peptides are injected into mice via tail-vein, and mice are sacrificed at the time points corresponding with data from previous biodistribution studies (2 min to 2 hr). In addition to brain tissues, liver, and kidney are removed (liver and kidney are used to evaluate their metabolic stability in more stringent in vivo environments), sonicated, extracted and analyzed through radio-TLC and HPLC. The $^{99m}$Tc-labeled peptides and dual-labeled peptides that remain non-metabolized through this rigorous analysis can then be investigated further in animal models.

Example 14

Bioassays

1. Preparation of Aβ Fibrils

In vitro binding assays are performed to evaluate interactions of radiolabeled probes with Aβ1-40/42 using standard procedures as described in literature (Zhuang et al., 2003). Briefly, commercially available amyloid peptide is aggregated in solution by gently dissolving the peptide (433 μg, 100 μM) in PBS (1 ml, pH 7.4). The solution is incubated for 36-48 h at 37° C. with gentle and constant shaking to avoid gel formation at the meniscus. The stock solution is diluted 1:50 (to 2 μM) with PBS, pH 7.4. The aggregated peptide suspension is kept frozen at −80° C. until needed (the suspension does not show any noticeable change in properties for at least 8 weeks). The aggregated stock suspensions are continuously stirred to maintain a homogenous suspension during removal of aliquots for binding assays.

2. Binding Assays to Preformed Aβ Fibrils.

Binding assays to preformed fibrils are performed using procedures as described in the literature (Klunk et al., 2001). Briefly, prior to binding assays, the stock solution (2 μM) is thawed. To aliquots of this stock solution, radiolabeled peptide is added at various concentrations to a final concentration of 200 nM Aβ fibrils. After incubation, the bound radiolabel is separated from unbound probe through Centricon filters (100 kDa cut off) using a centrifuge. The amount of activity incorporated in the fibrils is measured through γ-counting using previously published procedures (Zhen et al., 1999). For inhibition assays, increasing concentration of inhibitor is added to a solution of fibrils containing radiolabeled peptide in a buffer solution. The mixture is incubated at room temperature for 1.5 h, and the aggregate-bound $^{99m}$Tc-peptide and free radioactivity is separated by filtration through Centricon filtration units using a centrifuge. The aggregate-bound $^{99m}$Tc-peptide collected on filters is counted in a γ-counter. Inhibition constants ($K_i$) are calculated as described previously (Han et al., 1996).

Example 15

Autoradiography of Brain Sections

Procedures well known in the art are used for auto-radiography and fluorescent staining experiments (Zhuang et al., 2003). Briefly, brains of transgenic APPsw+/− mice (obtained from Taconic; 12-15 months old) are removed and frozen in powdered ice (Zhuang et al., 2003). After equilibration to −20° C., consecutive 20-μm coronal sections are cut on a cryostat, thaw-mounted on Fisher-Superfrost slides and stored at −80° C. until needed. For experiments, sections are thawed, labeled with radiolabeled probe at room temperature for 1 h, washed with $Li_2CO_3$ dissolved in ethanol (40%), ethanol (40%; 2 min) and water (30 s). After drying, labeled sections are exposed to Cronex MRF film for 72 h. The films are developed and digitized using a computer based image analysis system (NIH image, version 1.61). The presence of radiolabeled plaques in the same tissue sections are confirmed with fluorescent staining using thioflavin-S (TF-S) through the following steps: a) staining with TF-S (0.0125% thioflavin-S in ethanol:PBS (40:60) for 3 minutes; b) sections are quickly washed in ethanol:PBS (1:1) for 3 min; PBS (1 min); water (1 min); and c) imaging of tissues using fluorescence. This process assists in evaluating the ability of BBB permeant Aβ-targeted peptides to label amyloid plaques ex-vivo. To confirm autoradiography results, brain sections are stained using thioflavin-S or other fluorophores to support or discard data obtained through autoradiography.

Example 16

Staining and Immunohistochemistry of Brain Tissues

Staining experiments with fluorescent Aβ-targeted probes are performed using procedures as previously described (DeMattos et al., 2002). Briefly, serial 40-μm tissue sections (brains of APPsw+/− and WT mice) are cut in the coronal plane on a freezing sliding microtome from genu of the corpus callosum through the caudal extent of the hippocampus. The sections are incubated with fluorescent-labeled peptides in an increasing concentration as a function of time to determine an optimal concentration using previously established procedures. Briefly, tissues sections are permeabilized with PBS-Trinitron-X-100, quenched for autofluorescence (10 mM $CuSO_4$ in 50 mM ammonium acetate), washed (3 times with PBS-Triton-X-100), followed by wash (3-times with PBS), incubated with fluorescent probe, washed with PBS, mounted (Vectashield media w/DAPI), sealed with nail polish, and analyzed on a Zeiss LSM 5 PASCAL confocal system coupled to a Zeiss Axiovert 200 microscope. Sections are analyzed to identify BBB permeant Aβ-targeted peptides that produce optimal staining at the lowest concentration of peptide.

Similarly, tissue sections from APPsw+/− and WT mice are processed with Aβ antibody. Briefly, tissue sections are permeabilized with PBS-Trinitron-X-100, quenched for autofluorescence (10 mM $CuSO_4$ in 50 mM ammonium acetate), washed (3 times with PBS-Triton-X-100), followed by another wash (3-times with PBS), treated with 3% milk-PBS, binding of Aβ using rabbit-anti-pan-Aβ-antibody (Biosource International), washed again (1% milk-PBS), visualized using anti-rabbit antibody conjugated with Alexa 568 (Molecular probes), washed (PBS), mounted (Vectashield media w/DAPI), sealed with nail polish, and analyzed on a Zeiss LSM 5 PASCAL confocal system coupled to a Zeiss Axiovert 200 microscope. While stained brain tissue sections of APPsw+/− serve as positive controls, the non-stained tissue sections from brains of WT mice provide negative controls.

Fluorescent BBB permeant Aβ-targeted peptides are expected to stain Aβ in cortical and hippocampal brain sections of APPsw+/− transgenic mice compared to none in WT controls. Experiments are performed using a range of concentrations of fluorescent BBB permeant Aβ-targeted peptides. Again, sections are analyzed to identify BBB permeant Aβ-targeted peptides that produce optimal staining at the lowest concentration of peptide.

Example 17

Bio-distribution and Pharmacokinetic Studies of Tc-99m-labeled BBB Permeant Aβ-targeted Peptides in Normal and Transgenic APPsw+/− Mice Tissue distribution and kinetics of the novel technetium-99m-labeled BBB permeant Aβ-targeted peptides in normal and transgenic mice is of interest. Because of the ease with which these agents can be labeled with technetium-99m using the methods described above, we can readily perform biodistribution in normal rats or mice. Briefly, control mice (Taconic) or transgenic APPsw+/− mice (Taconic) are anesthetized by isoflurane inhalation and injected with $^{99m}$Tc-peptide (2 μCi in 50-100 μl saline) via bolus injection through a tail vein. Animals are sacrificed by cervical dislocation at 5, 30, 60, and 120 min post-injection (n=2-4). The brains are immediately removed and dissected into cerebellum and remaining whole brain (including brain stem) fractions prior to weighing and counting to evaluate regional differences in the location of radiotracer in comparison with APP formation. Blood samples are obtained by cardiac puncture and tissues are harvested rapidly and weighed. Gamma activities in organ samples are counted for 1 minute or until two standard deviations of sampling are below 0.5%. Data are expressed as percent of injected dose (% ID) per organ [(organ μCi) (injected μCi)$^{-1}$×100] or % ID per gram of tissue [(tissue μCi) (injected μCi)$^{-1}$ (g tissue)$^{-1}$×100].

These procedures provide data for pharmacokinetic analysis in general, and evaluation of BBB permeant Aβ-targeted peptides for the ability to permeate the BBB in particular. In the absence of the target, radiolabeled probes are likely to demonstrate moderate uptake in brains of control mice, followed by complete wash out of activity resulting in a low background signal. However, in the presence of targeted plaques in transgenic APP mice, enhanced accumulation and retention in brains is expected to provide non-invasive imaging of mice.

Example 18

Imaging Studies

Both control and APPsw+/− mouse models of matching age are used for SPECT/PET imaging. The APPsw+/− mouse is commercially available from Taconic (Hsiao et al., 1996). The mouse model carries a transgene coding for the 695-amino acid isoform of human Alzheimer's β-amyloid precursor protein (APP) derived from a large Swedish family with early-onset of AD. The mouse expresses a high concentration of the mutant Aβ, develops significant amyloid plaques, and displays memory deficits. Transgenic mice and their appropriate control animals (11-13 months old) are anesthetized with isoflurane inhalation. Optimized BBB permeant, $^{99m}$Tc-Aβ-targeted peptides or dual-labeled BBB permeant Aβ-targeted peptides (1-2 mCi dissolved in 100 μl saline) are injected via a tail vein into mice. For producing scintigraphic images using novel $^{99m}$Tc-peptides, mice are positioned under a gamma scintillation camera (Siemens Basicam, Siemens Medical Systems, Iselin, N.J.; 5 mm pinhole collimator; 20% energy window centered over 140 keV photopeak of technetium-99m). Sequential posterior images of mice are collected at one frame/minute for 2-120 min with a 128×128 matrix and corrected for radioactive decay. Brain accumulation of $^{99m}$Tc-peptides are analyzed by manually drawing regions of interest over the brain parenchyma and subtracting background radioactivity determined from a region of interest placed adjacent to the head of each mouse. For producing $^{94m}$Tc- and $^{64}$Cu-peptide PET images, mice are positioned in MicroPET detector R4 (Concorde Microsystems, Knoxyille, Tenn.) and imaged (10 min acquisition time; 1 bed position; filtered-back projection reconstruction; isotropic image resolution 1.8 mm). MicroPET images are corrected for decay.

Other Embodiments

When introducing elements of the present invention or the preferred embodiments thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

REFERENCES

Albericio, F., Bofill, J., El-Faham, A. and Kates, S. (1998) Use of onium salt-based coupling reagents in peptide synthesis. *J Org Chem*, 63, 9678-9683.

Arpicco, S., Dosio, F., Brusa, P., Crosasso, P. and Cattel, L. (1997) New coupling reagents for the preparation of disulfide cross-linked conjugates with increased stability. *Bioconjug Chem*, 8, 327-337.

Atherton, E. and Sheppard, R. (1989) Solid phase peptide synthesis: A practical approach, IRL Press, Oxford, UK.

Babich, J. W. a. F., A. J. (1995) Effect of "co-ligand" on the biodistribution of 99 mTc-labeled hydrazino nicotinic acid derivatized chemotactic peptides. *Nucl Med Biol*, 22, 25-30.

Barany, G., Albericio, F., Biancalana, S., Bontems, S., Chang, J. L., Eritja, R., Ferrer, M., Fields, C. and Fields, G. (1992) Biopolymer syntheses on novel polyethylene glycolpolystyrene (PEG-PS) graft supports, pp 603-604. In Peptides. Chem Biol, Proc. Am. Pept. Symp. (12th).

Bayer, E. and Rapp, W. (1986) New polymer supports for solid-liquid-phase peptide synthesis, pp 3-8. In chemistry of peptides and proteins, Voelter, W; Bayer E; Ovchinnkov Y A and Ivanov V T eds., Walterde Grayter & Co., Berlin.

Beyer, U., Roth, T., Schumacher, P., Maier, G., Unold, A., Frahm, A., Fiebig, H., Unger, C. and Kratz, F. (1998) Synthesis and in vitro efficacy of transferrin conjugates of the anticancer drug chlorambucil. *J Med Chem*, 41, 2701-2708.

Blomberg, K., Hurskainen, P. and Hemmilä, I. (1999) Terbium and rhodamine as labels in a homogeneous time-resolved fluorometric energy transfer assay of the β subunit of human chorionic gonadotropin in serum. *Clin Chem*, 45, 855-861.

Chan, W. C. and White, P. D. (2002) *FMOC Solid Phase Peptide Synthesis, A Practical Approach*, Oxford University Press, New York.

Dawson, R., Elliott, D., Elliot, W. and Jones, K. (1989) Data for Biochemical Research, 3rd Edition, Oxford University Press, Oxford, UK, pp 580.

Deguchi, Y., Kurihara, A. and Pardridge, W. (1998) Retention of Biologic Activity of Human Epidermal Growth Factor Following Conjugation to a Blood-Brain Barrier Drug Delivery Vector via an Extended Poly(ethylene glycol) Linker. *Bioconjug. Chem.*, 10, 32-37.

DeMattos, R., O'dell, M., Parsadanian, M., Holtzman, D. and et. al. (2002) Clusterin promotes amyloid plaque formation and is critical for neuritic toxicity in a mouse model of Alzheimer's disease. *Proc Natl Acad Sci USA*, 99, 10843-10848.

Devita, T., Hellman, S. and Rosenberg, S. (1997) Principles and Practice of Oncology, 5th Ed., J. B. Lippincott, Co., Phila, 1997, pp. 3125.

Devita, V. (1995) Biologic Therapy of Cancer, 2nd Ed., J. B. Lippincott, Co., Phila, 1995, pp. 919.

Dezutter, N., De Groot, T., Busson, R., Janssen, G. and Verbruggen, A. (1999a) Preparation of 99 mTc-N2S2 conjugates of Chrysamine G:potential probes for beta-amyloid protein of Alzheimer's disease. *J label Compd Radiopharm*, 42, 309-324.

Dezutter, N., Dom, R., deGroot, T., Bormans, G. and Verbruggen, A. (1999b) A probe for b-amyloid protein of Alzheimer's disease. *Eur J Nucl Med*, 26, 1392-1399.

Dirven, H., van Ommen, B. and van Bladeren, P. (1996) Glutathione conjugation of alkylating cytostatic drugs with a nitrogen mustard group and the role of glutathione S-Transferases. *Chem Res Toxicol*, 9, 351-360.

Dishino, D., Welch, M J, Kilbourn, M R, and Raichle, M E. (1983) Relationship between lipophilicity and brain extraction of C-11-labeled radiopharmaceuticals. *J Nuc Med*, 24, 1030-1038.

Drouillat, B., Hillery, A., Dekany, G., Falconer, R., Wright, K. and Toth, I. (1998) Novel liposaccharide conjugates for drug and peptide delivery. *J. Pharm. Sci.*, 87, 25-30.

Eckelman, W. C. (1995) Radiolabeling with technetium-99m to study high-capacity and low-capacity biochemical systems. *Eur J Nucl Med*, 22, 249-263.

Frisch, E., Boeckler, C. and Schuber, F. (1996) Synthesis of short polyoxyethylene-based heterobifunctional cross-linking reagents application to the coupling of peptides to liposomes. *Bioconjug Chem*, 7, 180-186.

Games, D. (1995) Alzheimer-type neuropathology in transgenic mice overexpressing V717F β-amyloid precursor protein. *Nature*, 373, 523-527.

Goodman, L., Gilman, A., Hardman, J. and Limbird, L. (1996) Goodman & Gilman's The Pharmacological Basis of Therapeutics, Ninth Edition, McGraw-Hill, New York.

Grant, G. A. (2002) *Evalution Of The Synthetic Product Synthetic Peptides, A User's Guide*, 2nd ed. Oxford University Press, New York.

Grummon, G., Rajagopalan, R., Palenik, G. J., Koziol, A. E. and Nosco, D. L. (1995) Synthesis, Characterization and Crystal Structures of Technetium(V)-Oxo Complexes Useful in Nuclear Medicine. 1. Complexes of Mercaptoacetylglycylglycylglycine (MAG3) and Its Methyl Ester Derivative (MAG3OMe). *Inorg Chem*, 34, 1764-1772.

Han, H., Cho, C. and Lansbury, P. J. (1996) Technetium complexes for quantification of brain amyloid. *J Am Chem Soc*, 118, 4506-4508.

Holtzman, D., Bales, K., Tenkova, T., Paul, S. and et. al. (2000) Apolipoprotein E isoform-dependent amyloid deposition and neuritic degeneration in a mouse model of Alzheimer's disease. *Proc Natl Acad Sci USA*, 97, 2892-2897.

Hom, R. and Katzenellenbogen, J. (1997) Technetium-99m-labeled receptor-specific small-molecule radiopharmaceuticals: recent developments and encouraging results. *Nucl Med Biol*, 24, 485-498.

Hoover, J. (1975) Remington's Pharmaceutical Sciences, Mack Publishing Co., Easton, Pa.

Houghten, R. A. (1985) General method for the rapid solid-phase synthesis of large numbers of peptides: specificity of antigen-antibody interaction at the level of individual amino acids. *Proc. Natl. Acad. Sci. USA,* 82, 5131-5135.

Hsiao, K., Chapman, P., Nilsen, S., Eckman, S., Harigaya, Y., Younkin, S., Yang, F. and Cole, G. (1996) Correlative memory deficits, Aβ elevation, and amyloid plaques in transgenic mice. *Science,* 274, 99-102.

Jamieson, E., Jacobson, M., Barnes, C., Chow, C. and Lippard, S. (1999) Structural and Kinetic studies of a cisplatin-modified DNA Icosamer binding to HMG1 Domain B. *J Biol Chem,* 274, 12346-12354.

Jurisson, S., Berning, D., Jia, W. and Ma, D.-S. (1993) Coordination compounds in nuclear medicine. *Chem Rev,* 93, 1137-1156.

Kempe, M. and Barany, G. (1996) CLEAR: A Novel Family of Highly Cross-Linked Polymeric Supports for Solid-Phase Peptide Synthesis. *J. Am. Chem. Soc.,* 118, 7083-7093.

King, F. (1994) Medicinal Chemistry: Principles and Practise, Royal Society of Chemistry, Cambridge, UK, pp 313.

Klunk, W., Bacskai, B., Mathis, C., Kajdasz, S., Mclellan, M., Frosch, M., Debnath, M., Holt, D., Wang, Y. and Hyman, B. (2002) Imaging Ab plaques in living transgenic mice with multiphoton microscopy and methoxy-X04, a systemically administered congo red derivative. *J Neuropathol Exp Neurol,* 61, 797-805.

Klunk, W., Wang, Y., Hunag, G., Debnath, M., Holt, D. and Mathis, C. (2001) Uncharged thioflavin-T derivatives bind to amyloid-beta protein with high affinity and readily enter the brain. *Life Sci,* 69, 1471-1484.

Kowall, N., Mckee, A., Yanker, B. and Beal, M. (1992) In vivo neurotoxicity of b-amyloid (1-40) and b(25-35) fragment. *Neurobiol Aging,* 13, 537-542.

Kung, M., Hou, C., Zhuang, Z., Zhang, B., Skovronsky, D., Trojanowski, J., Lee, V. and Kung, H. (2002) IMPY: an improved thioflavin-T derivative for in vivo labelling of b-amyloid plaques. *Brain Res,* 956, 202-210.

Kyte, J. and Doolittle, R. F. (1982) A simple method of displaying the hydropathic character of a protein. *J. Mol. Biol.,* 157, 105-132.

Lansbury, P. J. (1996) A reductionist view of Alzheimer's disease. *Acc Chem Res,* 29, 317-321.

Lemere, C. and et. al. (1996a) The E280A presenilin1 Alzheimer mutation produces increased Aβ42 deposition and severe cerebellar pathology. *Nature Med,* 2, 1146-1148.

Lemere, C. et. al. (1996b) Sequence of deposition of heterogenous amyloid β-peptides and Apo-E in Down Syndrome: Implications for initial events in amyloid plaque formation. *Neurobiol Disease,* 3, 16-32.

Li, H., Jiang, X., Ye, Y., Fan, C., Todd Romoff, T. and Goodman, M. (1999) 3-(Diethoxyphosphoryloxy)-1,2,3-benzotriazin-4(3H)-one (DEPBT): A new coupling reagent with remarkable resistance to racemization. *Organic Letters,* 1, 91-94.

Liberman, H. and Lachman, L. (1980) Pharmaceutical Dosage Forms, Marcel Decker, New York, N.Y.

Lin, Y., Caporaso, G., Chang, P., Ke, X. and Tam, J. (1988) Synthesis of a biological active tumor growth factor from the predicted DNA sequence of Shope fibroma virus. *Biochemistry,* 27, 5640-5645.

Lister-James, J., Knight, L. C., Maurer, A. H., Bush, L. R., Moyer, B. R. and Dean, R. T. (1996) Thrombus imaging with a technetium-99m-labeled activated platelet receptor-binding peptide. *J Nucl Med,* 37, 775-781.

Lister-James, J., Moyer, B. and Dean, R. (1997a) Pharmacokinetic considerations in the development of peptide-based imaging agents. *Q J Nucl Med,* 41, 111-118.

Lister-James, J., Vallabhajosula, S., Moyer, B., Pearson, D., McBride, B., De Rosch, M., Bush, L., Machac, J. and Dean, R. (1997b) Pre-clinical evaluation of technetium-99m platelet receptor-binding peptide. *J Nucl Med,* 38, 105-111.

Liu, C., Qureshi, I. A., Ding, X., Shan, Y., Huang, Y., Xie, Y. and Ji, M. (1996) Modulation of multidrug resistance gene (mdr-1) with antisense oligodeoxynucleotides. *Clin Sci* (Lond), 91, 93-98.

Liu, S. and Edwards, D. (1999) $^{99m}$Tc-labeled small peptides as diagnostic radiopharmaceuticals. *Chem Rev,* 99, 2235-2268.

Maisey, M., Britton, K. and Collier, D. (1998) Clinical Nuclear Medicine, Third Edition, Chapman & Hall Medical.

Majocha, R., Reno, J., Friedland, R., VanHaight, C., Lyle, L. and Marotta, C. (1992) Development of monoclonal antibody specific for b/A4 amyloid in Alzheimer disease brain for application to invivo imaging of amyloid angiopathy. *J Nucl Med,* 33, 2184-2189.

McKhann, G., et. al. (1984) Clinical diagnosis of Alzheimer's disease: a report of the NINCDS-ADRDA work group. *Neurology,* 34, 939-944.

Meegalla, S., Plossl, K., Kung, M.-P., Chumpradit, S., Stevenson, D., Kushner, S., McElgin, W., Mozley, P. and Kung, H. (1997) Synthesis and characterization of technetium-99m-labeled tropanes as dopamine transporter-imaging agents. *J. Med. Chem.,* 40, 9-17.

Meldal, M. (1992) Pega: a flow stable polyethylene glycol dimethyl acrylamide copolymer for solid phase synthesis. *Tetrahedron Lett.,* 33, 3077-3080.

Merrifield, R., Vizioli, L. and Boman, H. (1982) Synthesis of the antibacterial peptide cecropin A (1-33). *Biochemistry,* 21, 5020-5031.

Mroczkowsa, J., Roux, F., Nalecz, M. and Nalecz, K. (2000) Blood-brain barrier controls carnitine levels in the brain: A study on a model system with RBE4 cells. *Biochem Biophys Res Commun,* 267, 433-437.

Papadopoulos, M., Chiotellis, E., Varvarigou, A., Mastrostamatis, S., Cotsyfakis, C., Vavouraki, H. and Stathaki, S. (1993) Correlation of lipophilicity to biodistribution of 99mTc-labelled aminothiols. *Nucl. Med. Biol.,* 20, 101-104.

Pennington, M. and Dunn, B. (1994) *Peptide Synthesis Protocol: Methods In Molecular Biology* 35, Humana Press, Totowa.

Poduslo, J., Wengenack, T., Curran, G., Wisniewski, T., Sigurdsson, E., Macura, S., Borowski, B. and Jack, C. J. (2002) Molecular targeting of Alzheimer's amyloid plaques for contrast-enhanced magnetic resonance imaging. *Neurobiol Disease,* 11, 315-329.

Polyakov, V., Sharma, V., Dahlheimer, J., Pica, C., Luker, G. and Piwnica-Worms, D. (2000) Novel Tat-peptide chelates for direct transduction of technetium-99m and rhenium into human cells for imaging and radiotherapy. *Bioconjug Chem,* 11, 762-771.

Prantner, A., Sharma, V. and Piwnica-Worms, D. (2003) Synthesis and characterization of a Gd-DOTA D-permeation peptide for magnetic resonance relaxation enhancement of intracellular targets. *Molec Imaging,* 2, 333-341.

Rajagopalan, R., Grummon, G., Bugaj, J., Hallemann, L., Webb, E., Marmion, M., Vanderheyden, J.-L. and Srinivasan, A. (1997) Preparation, characterization, and biological evaluation of technetium(V) and rhenium(V) complexes of novel heterocyclic tetradentate $N_3S$ ligands. *Bioconjugate Chem,* 8, 407415.

Scheuner, D. and al., e. (1996) Secreted amyloid β-protein similar to that in the senile plaques of Alzheimer's disease is increased in vivo by the presenilin 1 and 2 and APP mutations linked to familial Alzheimer's disease. *Nature Med,* 2, 864-870.

Schumock, G. (1998) Economic considerations in the treatment and management of Alzheimer's disease. *Am J Health Syst Pharm*, 55(suppl.2), S17-S22.

Selkoe, D. (1997) Alzheimer's disease: genotype, phenotype, and treatments. *Science*, 275, 630-631.

Skovronsky, D., Zhang, B., Kung, M.-P., Kung, H., Trojanowsky, J. and Lee, V. (2000) In vivo detection of amyloid plaques in a mouse model of Alzheimer's disease. *Proc Natl Acad Sci USA*, 97, 7609-7614.

Stark, D. and Bradley, W. (1988) Magnetic Resonance Imaging, C. V. Mosby Co., St. Louis, Mo. pp 1516.

Teller, J. (1996) Presence of soluble amyloid β-peptide precedes amyloid plaque formation in Down's syndrome. *Nature Med*, 2, 93-95.

Tjernberg, L., Lilliehook, C., Callaway, D., Naslund, J., Hahne, S., Thyberg, J., Terenius, L. and Nordstedt, C. (1997) Controlling amyloid b-fibril formation with protease-stable ligands. *J Biol Chem*, 272, 12601-12605.

Trimble, S., Marquardt, D. and Anderson, D. (1997) Use of designed peptide linkers and recombinant hemoglobin mutants for drug delivery: In vitro release of an angiotensin II analog and kinetic modeling of delivery. *Bioconjug Chem*, 8, 416-423.

Ubarretxena-Belandia, I., Hozeman, L., van der Brink-van der Laan, E., Pap, E., Egmond, M., Verheij, H. and Dekker, N. (1999) Outer membrane phospholipase A is dimeric in phospholipid bilayers: A cross-linking and fluorescence resonance energy transfer study. *Biochemistry*, 38, 7398-7405.

Violini, S., Sharma, V., Prior, J., Dyszlewski, M. and Piwnica-Worms, D. (2002) Evidence for a plasma membrane-mediated permeability barrier to Tat basic domain in well-differentiated epithelial cells: lack of correlation with heparan sulfate. *Biochemistry*, 41, 12652-12661.

Wadghiri, Y., Sigurdsson, E., Sadowski, M., Elliot, J., Li, Y., Scholtzova, H., Tang, C., Aguinaldo, G., Pappolla, M., Duff, K., Wisniewski, T. and Turnbull, D. (2003) Detection of Alzheimer's amyloid in transgenic mice using magnetic resonance microimaging. *Magn Reson Med*, 50, 293-302.

Walker, L., Price, D., Voytko, M. and Schenk, D. (1994) Labeling of cerebral amyloid in vivo with a monoclonal antibody. *J Neuropathol Exp Neurol*, 53, 377-383.

Weiner, M. (1997) Alzheimer's disease: diagnosis and treatment. *Harvard Rev. Psychiatry*, 4, 306-316.

Weissleder, R., Moore, A., Mahmood, U., Bhorade, R., Benveniste, H., Chicocca, E. and Basilion, J. (2000) In vivo magnetic resonance imaging of transgene expression. *Nat Med*, 6, 351-355.

Wengenack, T., Curran, G. and Poduslo, J. (2000) Targeting Alzheimer amyloid plaques invivo. *Nat Biotech*, 18, 868-872.

Wen-hong, L., Fraser, S. and Meade, T. (1999) A calcium-sensitive magnetic resonance imaging contrast agent. *J Am Chem Soc*, 121, 1413-1414.

Wong, E., Fauconnier, T., Bennett, S., Valliant, J., Nguyen, T., Lau, F., Lu, L., Pollak, A., Bell, R. and Thornback, J. (1997) Rhenium(V) and technetium(V) oxo complexes of an $N_2N'S$ peptidic chelator: evidence of interconversion between the syn and anti conformations. *Inorg Chem*, 36, 5799-5808.

Wong, S. (1991) Chemistry of Protein Conjugation and Cross-linking, CRC press, Boca Raton, pp 328.

Yanker, B. (1996) Mechanisms of neuronal degeneration in Alzheimer's disease. *Neuron*, 16, 921-932.

Zhen, W., Han, H., Anguiano, M., Lernere, C., Cho, C. and Lansbury, P. J. (1999) Synthesis and amyloid binding properties of rhenium complexes: preliminary progress towards a reagent for SPECT imaging of Alzheimer's disease brain. *J Med Chem*, 42, 2805-2815.

Zhuang, Z., Kung, M., Wilson, A., Lee, C., Plossl, K., Hou, C., Holtzman, D. and Kung, H. (2003) Structure-activity relationships of imidazo[1,2-a]pyridines as ligands for detecting amyloid plaques in the brain. *J Med Chem*, 46, 237-243.

---

What is claimed is:

1. A compound comprising:
   a blood brain barrier (BBB)-permeant, Aβ-targeting peptide comprising an amino acid sequence of SEQ ID NO: 1; and
   a chelation core;
   wherein the Aβ-targeting peptide is coupled to the chelation core.

2. A compound in accordance with claim 1 wherein said chelation core comprises a medical imaging agent.

3. A compound in accordance with claim 1 wherein said chelation core has the structure of Formula I:

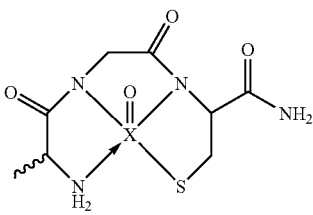

wherein X is one of technetium-99m, technetium 94m and rhenium.

4. A compound in accordance with claim 1 wherein said chelation core has a structure selected from the group consisting of:

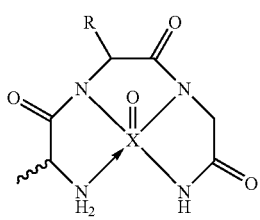

R = OH, COOH, (CH₂)₄NH₂

Formula I, wherein X is one of technetium-99m, technetium 94m and rhenium;

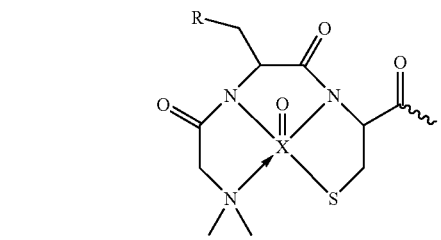

R = OH, COOH, (CH₂)₃NH₂

Formula II, wherein X is one of technetium-99m, technetium 94m and rhenium;

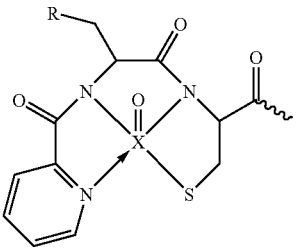

R = OH, COOH, (CH₂)₃NH₂

Formula III, wherein X is one of technetium-99m, technetium 94m and rhenium; and

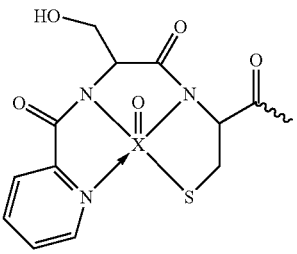

Formula IV, wherein X is one of technetium-99m, technetium-94m and rhenium.

5. A diagnostic composition for imaging amyloid deposits, comprising:
   the compound in accordance with claim 1;
   a medical imaging agent selected from the group consisting of a radionuclide, a relaxivity metal, a fluorochrome, a dye, and an enzyme substrate, and
   a pharmaceutically acceptable excipient or diluent;
   wherein the medical imaging agent is coupled to said chelation core.

6. A diagnostic composition in accordance with claim 5 wherein said medical imaging agent comprises a radioisotope.

7. A diagnostic composition in accordance with claim 5 wherein said medical imaging agent comprises technetium-99m.

8. A diagnostic composition in accordance with claim 5 wherein said medical imaging agent comprises technetium-94m.

9. A diagnostic composition in accordance with claim 5, comprising a radionuclide or a relaxivity metal, said radionuclide or relaxivity metal coordinated to said chelation core.

10. A diagnostic composition in accordance with claim 9, wherein said chelation core is selected from the group consisting of DTPA, EDTA, DOTA, TETA and ε-KGC amide.

11. A diagnostic composition in accordance with claim 9, comprising a radionuclide wherein said radionuclide is a radioactive isotope of a metal selected from the group consisting, of: Tc, Ru, In, Ga, Co, Pt, Fe, Os, Ir, W, Re, Cr, Mo, Mn, Ni, Rh, Pd, Nb, Cu, and Ta.

12. A diagnostic composition in accordance with claim 9, comprising a relaxivity metal wherein said relaxivity metal is a paramagnetic isotope of a metal selected from the group consisting of Mn, Cr, Fe, Gd, Eu, Dy, Ho, Cu, Co, Ni, Sm, Tb, Er, Tm, and Yb.

* * * * *

SEQUENCE LISTING

<160> NUMBER OF SEQ ID NOS: 2

<210> SEQ ID NO 1
<211> LENGTH: 10
<212> TYPE: PRT
<213> ORGANISM: Artificial
<220> FEATURE:
<223> OTHER INFORMATION: BBB-permeant peptide sequence with ability to bind Aa

<400> SEQUENCE: 1

Lys Lys Leu Val Phe Phe Ala Lys Gly Cys
1               5                   10

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile

-continued

```
                20              25              30
Gly Leu Met Val Gly Gly Val Val
            35              40
```